US012793840B2

(12) United States Patent
Lambrecht et al.

(10) Patent No.: US 12,793,840 B2
(45) Date of Patent: Nov. 10, 2026

(54) SYSTEMS AND METHODS FOR SELECTING ASSIGNMENTS FOR MANIPULATOR ASSEMBLIES

(71) Applicant: INTUITIVE SURGICAL OPERATIONS, INC., Sunnyvale, CA (US)

(72) Inventors: Bram Gilbert Antoon Lambrecht, Redwood City, CA (US); John Ryan Steger, Sunnyvale, CA (US)

(73) Assignee: INTUITIVE SURGICAL OPERATIONS, INC, Sunnyvale, CA (US)

( * ) Notice: Subject to any disclaimer, the term of this patent is extended or adjusted under 35 U.S.C. 154(b) by 436 days.

(21) Appl. No.: 18/007,027

(22) PCT Filed: Jul. 27, 2021

(86) PCT No.: PCT/US2021/043324
§ 371 (c)(1),
(2) Date: Jan. 26, 2023

(87) PCT Pub. No.: WO2022/026473
PCT Pub. Date: Feb. 3, 2022

(65) Prior Publication Data

US 2023/0290495 A1 Sep. 14, 2023

Related U.S. Application Data

(60) Provisional application No. 63/057,867, filed on Jul. 28, 2020.

(51) Int. Cl.
*G16H 40/63* (2018.01)
*G16H 40/40* (2018.01)

(52) U.S. Cl.
CPC ............. *G16H 40/63* (2018.01); *G16H 40/40* (2018.01)

(58) Field of Classification Search
CPC ......... A61B 34/25; A61B 34/35; A61B 34/37; A61B 90/06; A61B 90/37; A61B 90/90;
(Continued)

(56) References Cited

U.S. PATENT DOCUMENTS 6,311,181 B1 10/2001 Lee et al.
6,331,181 B1 12/2001 Tierney et al.
(Continued)

FOREIGN PATENT DOCUMENTS

CN 110859671 A 3/2020
WO WO-2007111737 A2 10/2007
(Continued)

OTHER PUBLICATIONS

International Search Report and Written Opinion for Application No. PCT/US2021/043324, mailed Feb. 9, 2022, 18 pages.
(Continued)

*Primary Examiner* — Blake A Wood
(74) *Attorney, Agent, or Firm* — Artegis Law Group, LLP

(57) ABSTRACT

A manipulator device management system can include a manipulator device comprising a plurality of manipulator arms and a control system. The control system can have one or more processors configured to perform operations comprising: selecting, for a first manipulator arm of the plurality of manipulator assemblies, a first assignment from a plurality of assignments available to the first manipulator arm; and causing the first manipulator arm to adopt the first assignment. The first assignment can be available to at least two manipulator arms of the plurality of manipulator arms. The first assignment can designate at least one operating parameter selected from the group consisting of a location for the
(Continued)

first manipulator arm and a type of instrument to be used with the first manipulator arm.

14 Claims, 12 Drawing Sheets

(58) Field of Classification Search
CPC .... A61B 2017/00482; A61B 2034/252; A61B 2034/254; A61B 2034/256; A61B 2090/064; A61B 2090/066; A61B 2090/0803; A61B 2090/0804; A61B 2090/0818; G16H 20/40; G16H 40/40; G16H 40/63; G16H 40/67
See application file for complete search history.

(56) References Cited

U.S. PATENT DOCUMENTS

| | | | | |
|---|---|---|---|---|
| 6,625,214 | B1 | 9/2003 | Umehara et al. | |
| 7,725,214 | B2 | 5/2010 | Diolaiti | |
| 7,955,322 | B2 | 6/2011 | Devengenzo et al. | |
| 8,529,582 | B2 | 9/2013 | Devengenzo et al. | |
| 8,666,544 | B2 | 3/2014 | Moll et al. | |
| 8,823,308 | B2 | 9/2014 | Nowlin et al. | |
| 10,470,830 | B2 | 11/2019 | Hill et al. | |
| 10,786,329 | B2 | 9/2020 | Schuh et al. | |
| 11,259,870 | B2 | 3/2022 | Dimaio et al. | |
| 11,298,186 | B2 | 4/2022 | Chou et al. | |
| 12,133,702 | B2 | 11/2024 | Nowlin et al. | |
| 12,426,969 | B2 | 9/2025 | Lambrecht et al. | |
| 2002/0082612 | A1 | 6/2002 | Moll et al. | |
| 2004/0049205 | A1 | 3/2004 | Lee et al. | |
| 2007/0151390 | A1 | 7/2007 | Blumenkranz et al. | |
| 2011/0137337 | A1 | 6/2011 | Van Den Dool et al. | |
| 2015/0185729 | A1* | 7/2015 | Kuffner, Jr. | B25J 9/0084 700/248 |
| 2016/0256154 | A1 | 9/2016 | Shelton, IV et al. | |
| 2017/0165837 | A1 | 6/2017 | Asano et al. | |
| 2017/0304021 | A1* | 10/2017 | Hathaway | B65H 75/38 |
| 2017/0323578 | A1 | 11/2017 | Valentine et al. | |
| 2018/0001476 | A1* | 1/2018 | Tan | B61G 7/04 |
| 2018/0049816 | A1 | 2/2018 | Shelton, IV et al. | |
| 2018/0311005 | A1* | 11/2018 | Mccormick | A61B 34/25 |
| 2019/0059985 | A1 | 2/2019 | Shelton, IV et al. | |
| 2019/0175294 | A1 | 6/2019 | Abbott et al. | |
| 2019/0192245 | A1 | 6/2019 | Abbott et al. | |
| 2019/0201102 | A1 | 7/2019 | Shelton, IV et al. | |
| 2019/0207911 | A1 | 7/2019 | Wiener et al. | |
| 2019/0231461 | A1 | 8/2019 | Steger et al. | |
| 2019/0343597 | A1* | 11/2019 | Corpa De La Fuente | A61B 17/1626 |
| 2020/0045132 | A1 | 2/2020 | Kimball et al. | |
| 2020/0100846 | A1 | 4/2020 | Huang et al. | |
| 2020/0146765 | A1 | 5/2020 | Hibner et al. | |
| 2020/0170737 | A1 | 6/2020 | Bassik | |
| 2020/0214776 | A1 | 7/2020 | Hingwe et al. | |
| 2020/0222129 | A1 | 7/2020 | Gomez et al. | |
| 2020/0330174 | A1* | 10/2020 | Bertram | A61B 1/000096 |
| 2021/0045818 | A1 | 2/2021 | Asadian et al. | |
| 2021/0052335 | A1* | 2/2021 | Shuma | A61B 34/37 |
| 2021/0085410 | A1* | 3/2021 | Hassan | A61B 34/37 |
| 2021/0169593 | A1 | 6/2021 | Kapadia | |
| 2021/0212786 | A1 | 7/2021 | Kapadia et al. | |
| 2021/0220063 | A1 | 7/2021 | Kapadia et al. | |
| 2021/0338347 | A1 | 11/2021 | Kapadia et al. | |
| 2021/0393352 | A1 | 12/2021 | Seow et al. | |
| 2022/0039890 | A1 | 2/2022 | Waterbury et al. | |
| 2022/0039892 | A1 | 2/2022 | Waterbury et al. | |

FOREIGN PATENT DOCUMENTS

| | | | | |
|---|---|---|---|---|
| WO | WO-2015142801 | A1 | 9/2015 | |
| WO | WO-2016048738 | A1 | 3/2016 | |
| WO | WO-2016201313 | A1 | 12/2016 | |
| WO | WO-2017214243 | A1 | 12/2017 | |
| WO | WO-2018039459 | A1 | 3/2018 | |
| WO | WO-2018053305 | A1 | 3/2018 | |
| WO | WO-2018075527 | A1 | 4/2018 | |
| WO | WO-2018089819 | A2 | 5/2018 | |
| WO | WO-2018217431 | A1 | 11/2018 | |
| WO | WO-2019023020 | A1 * | 1/2019 | A61B 34/25 |
| WO | WO-2019032309 | A2 | 2/2019 | |
| WO | WO-2019133056 | A1 | 7/2019 | |
| WO | WO-2019164856 | A1 | 8/2019 | |
| WO | WO-2022013536 | A1 | 1/2022 | |

OTHER PUBLICATIONS

International Search Report and Written Opinion for Application No. PCT/US2021/043323, mailed Jan. 31, 2022, 28 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2021/043324 mailed Feb. 9, 2023, 12 pages.

* cited by examiner

SYSTEMS AND METHODS FOR SELECTING ASSIGNMENTS FOR MANIPULATOR ASSEMBLIES

CROSS-REFERENCES TO RELATED APPLICATIONS

The present application is a U.S. National Stage patent application of International Patent Application No. PCT/US2021/043324, filed Jul. 27, 2021, the benefit of which is claimed and claims priority to U.S. Provisional Patent Application No. 63/057,867 filed Jul. 28, 2020 and titled "Systems and Methods for Selecting Assignments for Manipulator Assemblies," the disclosure of each of which is incorporated herein by reference in its entirety.

TECHNICAL FIELD

The present technology generally relates to managing devices and, more specifically, to systems and methods for selecting assignments for components of, or drive elements of components of, computer-assisted devices.

BACKGROUND

Computer-assisted devices often comprise modular components that are disposable, reusable, interchangeable, etc. For example, such a device can comprise a manipulator assembly including one or more manipulator arms, each having one or more links connected by one or more joints. Such manipulator assemblies can be configured to be permanently or releasably mounted at or near a procedure site, such as mounted to a ceiling, a wall, a movable cart, an operating table, equipment used for the procedure, etc. In some cases, the manipulator assemblies are interchangeable at a procedure site, and a manipulator assembly can be positioned at various locations at a procedure site.

As another example of modularity, a computer-assisted device may be removably coupled to various instruments for specific applications and procedures. For example, the computer-assisted device may comprise manipulator assemblies with one or more manipulator arms, or other components configured to couple to the instruments. These instruments may also be interchangeable in that an instrument may be configured so that it can couple to different manipulator assemblies or other components of a given computer-assisted device. Use of different instruments can load or wear the manipulator arm(s) of manipulator assemblies, or the other computer-assisted device components, or the subcomponents of those components, in different ways. For example, certain uses or certain instruments may load or wear certain subcomponents more than other subcomponents. Accordingly, there is a need for systems and methods to improve use management of manipulator assemblies and other components or subcomponents of computer-assisted devices.

SUMMARY

In accordance with an embodiment of the present technology, a device management system can include a device comprising a plurality of manipulator arms. The device may comprise a medical or non-medical device. The management system can include a control system comprising one or more processors and a memory. The memory can include programmed instructions adapted to cause the one or more processors to perform operations comprising selecting, for a first manipulator arm of the plurality of manipulator arms, a first assignment from a plurality of assignments available to the first manipulator arm and causing the first manipulator arm to adopt the first assignment. In some embodiments, the first assignment is available to at least two manipulator arms of the plurality of manipulator arms. In some embodiments, the first assignment designates at least one operating parameter selected from the group consisting of: a location for the first manipulator arm and a type of instrument to be used with the first manipulator arm. In some embodiments, selecting the first assignment comprises: selecting from the plurality of assignments in a random or pseudorandom manner or selecting from the plurality of assignments based on historical data of the plurality of manipulator arms.

In accordance with further embodiments of the present technology, a device management system can include a plurality of manipulator arms comprising a first manipulator arm and a second manipulator arm. The management system can include a control system comprising one or more processors and a memory. The memory can include programmed instructions adapted to cause the one or more processors to perform operations comprising obtaining historical data of the plurality of manipulator arms, wherein the historical data comprises data selected from the group consisting of usage data and test data; selecting, for the first manipulator arm and based on the historical data, a first assignment from a plurality of assignments available to both the first manipulator arm and the second manipulator arm, the first assignment designating an operating parameter of the first manipulator arm; and selecting, for the second manipulator arm and based on the historical data, a second assignment from the plurality of assignments, the second assignment designating an operating parameter of the second manipulator arm.

In accordance with embodiments of the present technology, a device management system can include a control system comprising one or more processors and a memory. The memory can include programmed instructions adapted to cause the one or more processors to perform operations comprising: obtaining historical data of a plurality of manipulator arms, wherein the historical data comprises data selected from the group consisting of: usage data and test data; obtaining information about a medical procedure to be performed; and designating, based on the historical data and the information about the medical procedure, one or more manipulator arms the plurality of manipulator arms to be used in the medical procedure.

DESCRIPTION OF THE DRAWINGS

Many aspects of the present technology can be better understood with reference to the detailed description along with the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

In the specification, it should be appreciated that like reference numerals are used to identify like elements illustrated in one or more of the figures for purposes of illustrating embodiments of the present disclosure and not for purposes of limiting the same.

DETAILED DESCRIPTION

Figure 1A:
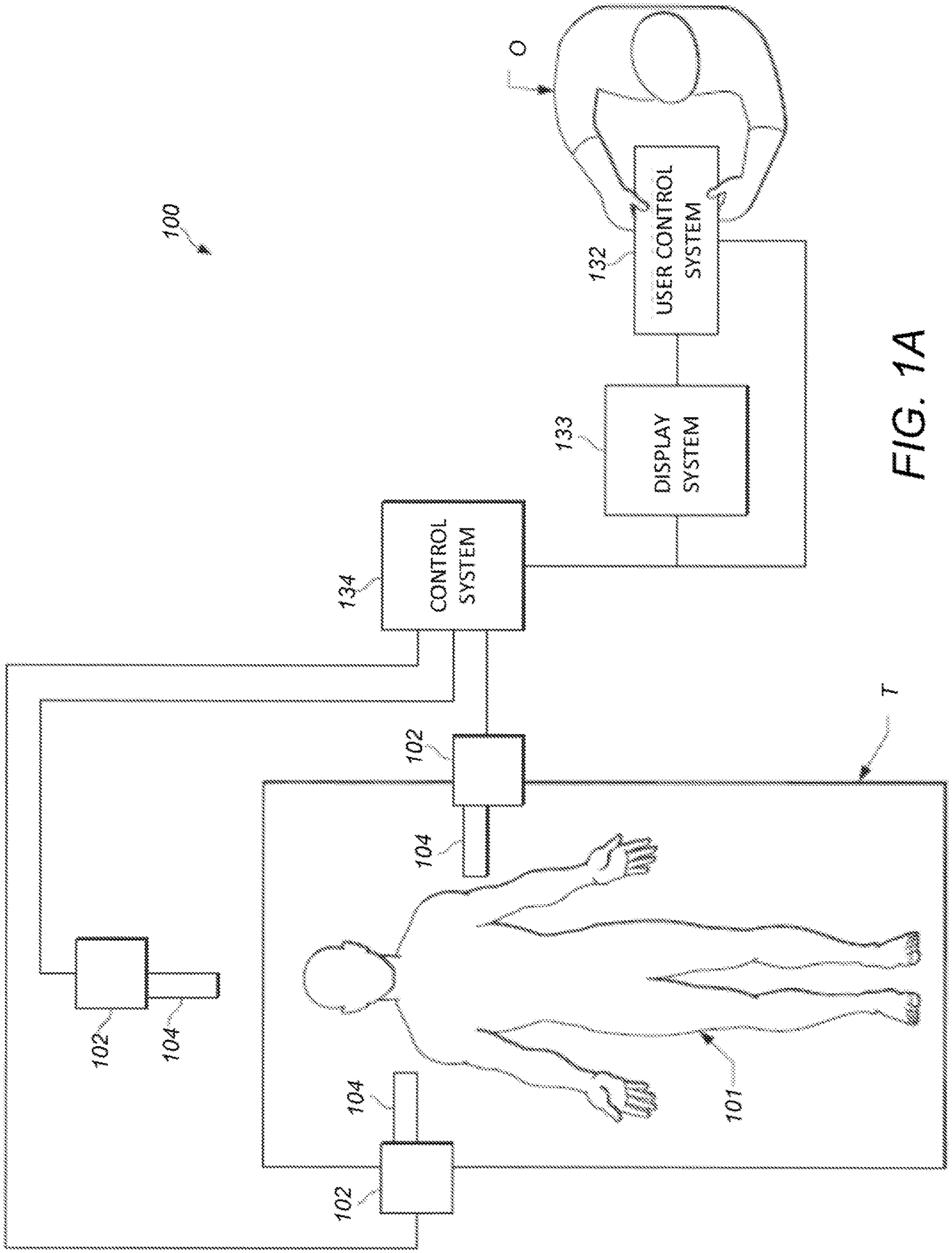
FIG. 1A is a schematic illustration of a device configured in accordance with an embodiment of the present technology.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely examples and are not to be considered as limiting the scope of the inventive aspects disclosed herein. In some embodiments, the instruments, systems, and methods described herein may be suitable for use in, for example, surgical, teleoperated surgical, diagnostic, therapeutic, or biopsy procedures. While some embodiments are provided herein with respect to such procedures, any reference to medical or surgical instruments and medical or surgical methods is intended as non-limiting. Thus, the instruments, systems, and methods described herein may be used for humans, animals, portions of human or animal anatomy, non-surgical diagnosis, as well as for industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

The present technology generally relates to systems and methods for selecting assignments for components of devices. Such devices can include, for example, computer-assisted medical devices having one or more manipulator assemblies, each having one or more manipulator arms (or other articulable structures, or other similar or appropriate structures) adapted to be operably coupled to one or more instruments (e.g., non-medical or medical instruments, manipulation instruments such as scissors, or imaging instruments such as cameras, or other apparatuses), installed in one or more locations, configured in one or more poses, and/or configured in one or more orientations. The various components of the devices described herein are subject to loading or wear over the course of time and over stages of the same procedure or over multiple procedures. Specific loading and wear can be attributed to many variables. These variables include, but are not limited to, the types of instruments used, the load types realized during procedures, overall component age, orientation of the manipulator arms and other components during a given procedure, orientation of the patient during a procedure, cleaning, reprocessing, services and maintenance, repair, and ambient conditions in the procedural and/or storage environments. For example, the type of instrument and/or type of procedure can result in specific types of loading on the components of the manipulator assemblies, manipulator arms, and/or instruments. Certain types of instruments and procedures can involve higher: frequency of loads, peak or average load magnitudes, load durations, peak or average momentums, peak or average torques or linear forces, ranges of motion, peak or average velocities or acceleration or jerks, numbers of direction reversals, number of actuations, durations of use, amounts of work, instantaneous or average power, peak or average temperatures or temperature ranges, frequency or number of temperature cycles, etc., than other procedures. Also, manipulator arm or instrument orientation can result in unique distribution of lubricants (e.g., sometime disadvantageous distribution) and/or unique gravity-induced loads on joints and other components. In some cases, the ambient environment can introduce unique wear to the system via humidity levels, temperature levels, ambient pressure (e.g., associated with altitude), and/or particulate (e.g., dust, sand, etc.) levels, and the like.

Types of loading or wear introduced by the above-described variables can include, but are not limited to, abrasion, corrosion, adhesion, thermal fatigue, mechanical fatigue, gouging, galling, fretting, pitting, brinelling, spalling, seizing, cracking (e.g., stress corrosion cracking), rusting, and creep/plastic deformation. The various types of loading or wear attributed to the above-listed variables can cause performance degradation or failures to different specific components, subcomponents of those components, and/or other portions of the devices. For example, loading or wear can be applied to drivetrain subcomponents such as actuators (e.g. motors, solenoids), bearings, drive cables, pulleys, gears; joint and link subcomponents. Wear and loading can be attributed to various operations performed by components/subcomponents. Example operations can include instrument movements, staple fires, cuts, ablations, clamps, etc.

In many cases, lower performance or failure of a subcomponent (e.g., of a manipulator arm or instrument) can lead to lower performance or failure of the entire component or larger device. For example, lower performance or failure of a drive assembly, sensor system, control system, or other system component or subcomponent of a manipulator arm can render the entire manipulator arm less capable or unusable without service or repair. Examples of drive assembly components include actuators and transmission systems. Examples of drive assembly subcomponents include drive elements configured to couple with and import motion or motive force (e.g., linear force or rotary torque) to parts of the manipulator arm or to input elements of an instrument, as well as drivetrain subcomponents coupled to drive the drive elements, such as cables, metal bands, drive screws, cable, gears and gear shafts, pulleys, levers, gimbals, actuators such as motors and solenoids, structural subcomponents such as chassis and devises, and other subcomponents of a drivetrain. Increased use of a component or a subcomponent, compared to use of other components or subcomponents, can lead to greater loading, greater wear, lower performance, or earlier failure of that component or subcomponent, as compared to the other components or subcomponents. It is thus advantageous to reduce over-use of components or subcomponents, as compared to other components or subcomponents, if such reduction is possible. As used herein, "couple," "coupled," or any form thereof, refer to connections between two or more components, whether directly (e.g., via direct contact) or indirectly (e.g., via one or more intermediate structures).

In order to reduce the variance in loading and wear between the components in the medical devices described herein, and thereby increase the overall performance or life of the device, various methods and systems can be implemented as described herein. The methods can, in some instances, include randomized or pseudorandomized assignment of manipulator arms for various tasks. The assignments can include couplings between types of instruments and manipulator arms, specific installation locations for the manipulator arms, and/or other operating parameters. In some implementations, the loads and wear of specific components can be monitored in order to assign instruments to less-used components (e.g., manipulator arms) of the device. For example, certain embodiments of the present technology can include manipulator arms with drive assemblies configured to couple with instruments. The drive assembly comprises a plurality of drive elements configured to cause movement of the instrument by driving a plurality of input elements of the instrument. In some instances, the drive elements of a given device are configured to couple with input elements of a variety of different instruments. The systems of the present technology can include one or more processors configured to execute instructions to manage the coupling between the devices and instruments to more evenly distribute loading or wear on the devices.

The present disclosure describes various instruments and portions of instruments in terms of their state in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (e.g., three degrees of rotational freedom, such as roll, pitch, and yaw). As used herein, the term "pose" refers to the position of an object or a portion of an object in at least one degree of translational freedom and to the orientation of that object or portion of the object in at least one degree of rotational freedom (e.g., up to six total degrees of freedom). As used herein, the term "shape" refers to a set of poses, positions, or orientations measured along an object.

FIG. 1A is a simplified diagram of a device in accordance with an embodiment of the present technology. Specifically, FIG. 1A illustrates a computer-assisted medical device 100. In some embodiments, the device 100 may be suitable for use in, for example, diagnostic, therapeutic, training, or other procedures regardless of if the procedures are surgical or non-surgical. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1A, the device 100 can include one or more manipulator assemblies 102. Although three manipulator assemblies 102 are illustrated in the embodiment of FIG. 1A, in other embodiments, more or fewer manipulator assemblies may be used. The exact number of manipulator assemblies will depend on the procedure and the space constraints within the operating room, among other factors. Each manipulator assembly 102 may comprise one or more manipulator arms (e.g., robotic manipulator arms). Multiple user control systems 132 may be co-located, or they may be positioned in separate locations. Multiple user control systems 132 can allow more than one operator to control one or more teleoperated manipulator assemblies in various combinations.

In this medical example, the manipulator assembly 102 is used to operate a medical instrument 104 (e.g., a manipulation, imaging, or other instrument) in performing various procedures on a patient 101. In some embodiments, one or more of the manipulator assemblies 102 includes more than one manipulator arm, and each manipulator arm is configured to have one or more medical instruments 104 mounted thereon. The instrument(s) 104 may be releasably or fixedly mounted to the manipulator assemblies. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. The manipulator assembly 102 may be configured to position and move the medical instrument 104 such that a distal portion of the manipulator assembly 102 and/or the medical instrument 104 pivots about a remote center of motion coincident with the instrument 104's entry aperture into the patient 101. The manipulator assembly 102 may then manipulate the instrument 104 to translate or rotate the instrument 104 in space, such as pivot the instrument 104 about the remote center of motion, insert or retract the instrument 104, and/or roll the instrument 104 about its shaft axis.

In some embodiments, the manipulator assembly 102 may be mounted to or near an operating table T (e.g., an examination or surgical table in a medical example). In such embodiments, the manipulator assembly 102 may be mounted directly to the table T or to a rail coupled to the table T. In various other embodiments, the manipulator assembly 102 may be mounted to a fixed or movable manipulating system (e.g., mounted to the floor, wall, or ceiling, or to a cart). The manipulating system may be separate from and spaced from the table T in the operating room. In such embodiments, the manipulating system may be independently movable relative to the table T. In such embodiments, one or more of the manipulator assemblies 102 may be mounted to any structure or in any manner as described above. For example, one manipulator assembly 102 may be mounted to the table T and another manipulator assembly 102 may be mounted to a manipulating system. In other examples, an additional manipulator assembly 102 may be mounted to the ceiling of the operating room.

Figure 1B:
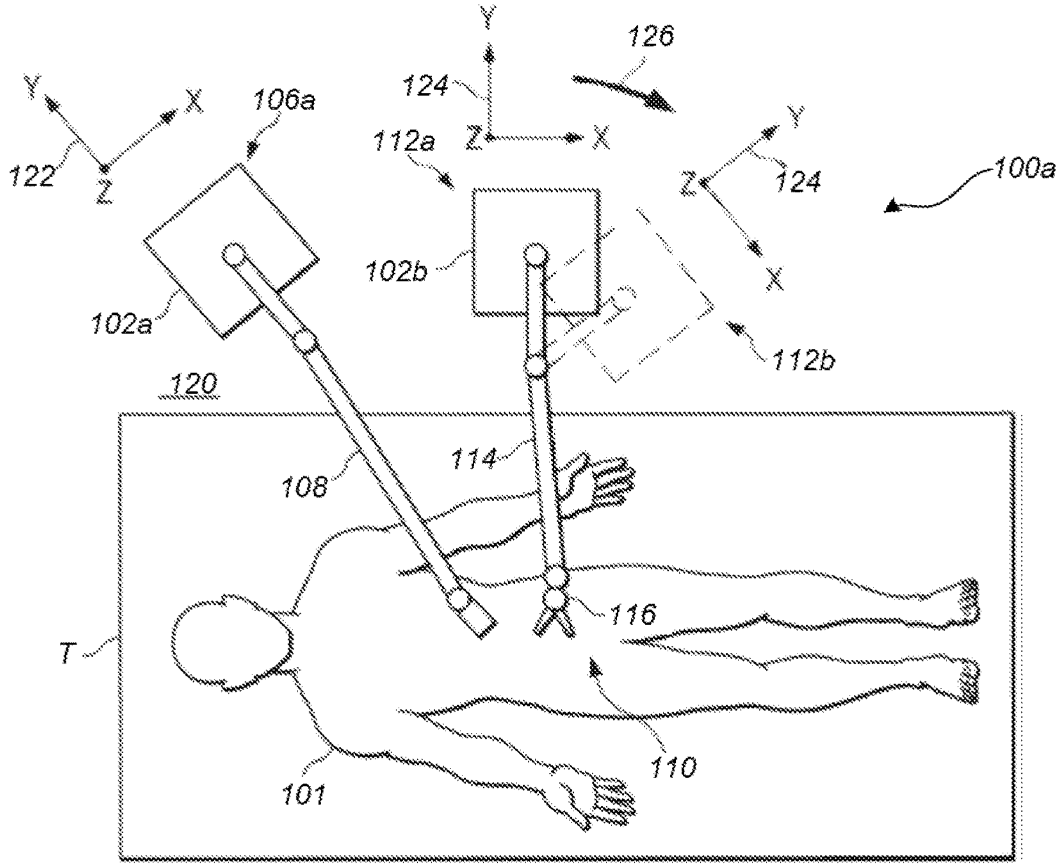
FIG. 1B is a schematic illustration of a device configured in accordance with another embodiment of the present technology, wherein manipulator assemblies of the medical device system are mounted to a movable support structure.
Figure 1C:
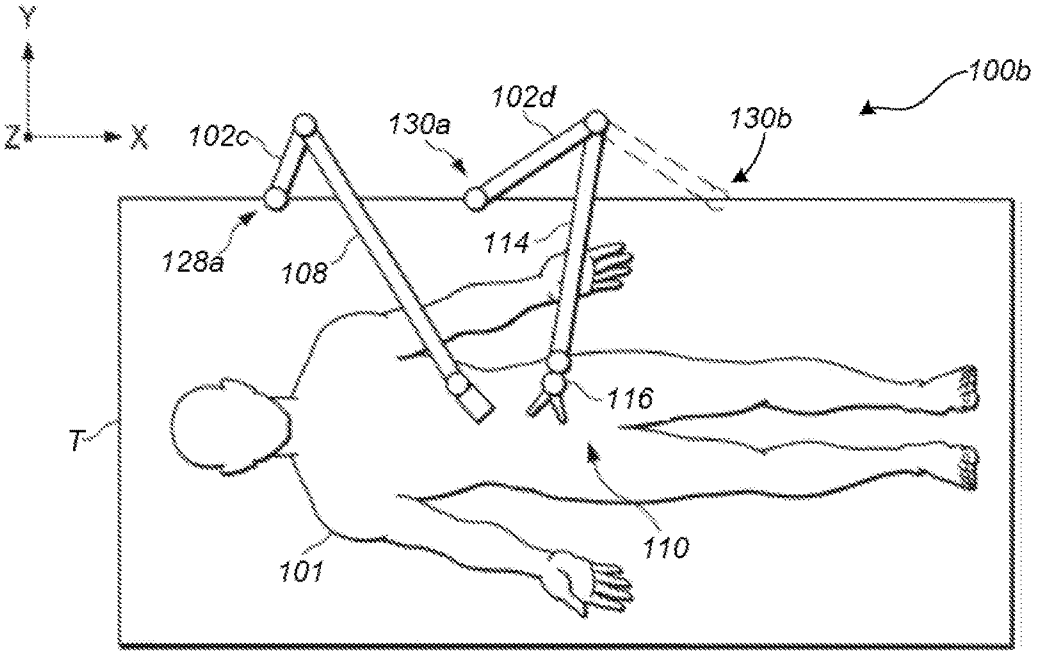
FIG. 1C is a schematic illustration of a device configured in accordance with another embodiment of the present technology, wherein manipulator assemblies of the medical device systems are mounted to a table.

FIGS. 1B and 1C illustrate two such example manipulator assembly configurations. More specifically, FIG. 1B is a schematic plan view of a medical device 100*a*, showing a patient and two patient-side units that illustrates an example situation in which separate instrument support structures are used during a medical procedure. The medical device 100*a* can share many or all of the characteristics of the medical device 100 described herein. The patient 101 is shown on a table T. An illustrative support structure 102*a* is shown as a mobile unit that can be moved across the operating room floor. The support structure 102*a* (e.g., a manipulator assembly) can support an instrument 108 such as an instrument comprising an endoscopic camera, which in the pose shown in FIG. 1B has a field of view (FOV) directed toward a work site 110 (e.g., a medical site such as a surgical site) within the patient 101. An illustrative support structure 102*b* (e.g., a manipulator assembly) is included, also shown as a mobile unit that can be moved across the operating room floor. The support structure 102*b* can support an instrument 114, such as a manipulation instrument posed to locate its end effector 116 at the work site 110. In various embodiments, each of the support structures 102*a*, 102*b* can replaced by one or multiple support structures. Further, each support structure (e.g. 102*a*, 102*b*) can be configured to support one or multiple instruments. The description that follows about the support structures 102*a* and 102*b* also applies to the various other support structures each may represent.

As shown in FIG. 1B, the support structure 102*a* is at a pose 106*a* relative to a world reference frame 120. The support structure reference frame 122 is associated with an individual link of the support structure's kinematic chain (e.g., a link of a setup structure, or a manipulator arm, or of a link of the instrument of support structure 102*a*) The support structure reference frame 122 orientation changes as the orientation of the associated individual link changes.

As further shown in FIG. 1B, the support structure 102*b* is at a first pose 112*a* with relative to the world reference frame 120. A support structure reference frame 124 is associated with an individual link of the support structure's kinematic chain. FIG. 1B further shows the support structure 102*b* at a second dotted-line pose 112*b* with reference to the world reference frame 120, which illustrates that the support structures 102*a*, 102*b* may be placed at and moved to various positions and orientations for and during operation. The reference frame 124 translates and rotates as its associated link translates and rotates, as shown by arrow 126.

FIG. 1C is another schematic plan view illustrating another example medical device configuration (e.g., medical device 100*b*). The medical device 100*b* can share many or all of the characteristics of the medical devices 100, 100*a* described herein. In FIG. 1C, the support structures 102*c*, 102*d* of the medical device are mounted to the table T. For example, the support structures 102*c*, 102*d* may be mounted at various positions along the table's top or side rail(s) or mounted to a base of the table. The support structure 102*c* (showing holding camera instrument 108) is mounted to the table T at a base position 128*a*. The support structure 102*d* (shown holding a manipulation instrument 114) is mounted to the table T at a base position 130*a*. FIG. 1C also illustrates via dotted lines the support structure 102*d* mounted to the table T at a base position 130*b*. This is to illustrate that the support structure 102*c*, 102*d* may be placed at or moved to various positions and orientations for and during operation.

In FIG. 1B, both the position and orientation of the tool support structure's base are shown changed, as reflected in the two poses 112*a*, 112*b*. In FIG. 1C, however, only the position of the tool support structure's base is shown changed, and the base orientation does not change as the table rail does not change orientation as the base changes positions along the rail. However, the tool support structure base position and orientation may change in other configurations, such as when the tool support structure is moved from one side of the table to the opposite side of the table. In addition, the table pose may change, which correspondingly changes the base orientation and position. Again, as discussed above, various combinations of support structures are possible. In some applications, the support structure that supports the first instrument 108 is either completely physically separate from the support structure that holds a second instrument 114 or is mechanically coupled via a shared support structure that also holds the second instrument 114 but without shared kinematic information and is therefore effectively kinematically separate.

Returning back to FIG. 1A, the device 100 can include a display system 133 for displaying an image or representation (e.g., a real-time image captured by an imaging instrument, a model derived from sensor data) of the work site and medical instrument 104. The display system 133 and the user control system 132 may be oriented so that an operator O (e.g., a surgeon or other clinician, as illustrated in FIG. 1A) can control the medical instrument 104 and the user control system 132 with the perception of telepresence. The image may be, for example, a two-dimensional or three-dimensional image captured by an imaging device of the work site. In some examples, the display system 133 may present images of the work site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images and/or as images from models created from the pre-operative or intra-operative image data sets.

The device 100 may also include control system 134. The control system 134 includes at least one memory and at least one computer processor (not shown) for effecting control between the medical instrument 104, the user control system 132, and the display system 133. The control system 134 also includes programmed instructions (e.g., a non-transitory machine-readable medium storing the instructions) to implement some or all the methods described in accordance with aspects disclosed herein, including instructions for providing information to display system 133. While the control system 134 is shown as a single block in the simplified schematic of FIG. 1A, the system may include one, two, or more data processing circuits with one portion of the processing optionally being performed on or adjacent to manipulator assembly 102, another portion of the processing being performed at user control system 132, and/or the like. Any of a wide variety of centralized or distributed data processing architectures may be employed. Similarly, the programmed instructions may be implemented as a number of separate programs or subroutines, or they may be integrated into a number of other aspects of the systems described herein. In one embodiment, the control system 134 supports wireless communication protocols such as Bluetooth, IrDA, HomeRF, IEEE 802.11, DECT, and Wireless Telemetry.

As mentioned above, the user control system 132 can allow the operator O to view the work site and to control the manipulator assembly 102. In some examples, the user control system 132 comprises an operator console, such as located in the same room as the table T. However, it is to be understood that the user control system 132 and operator O can be in a different room or a completely different building from the patient 101. The user control system 132 generally includes one or more input devices for controlling the manipulator assembly 102. The input devices may include any number of a variety of devices, such as joysticks, trackballs, data gloves, trigger-guns, hand-operated controllers, voice recognition devices, body motion or presence sensors, and/or the like. In some embodiments, the input devices are provided with the same degrees of freedom as the associated medical instrument 104. In some embodiments, the input devices may have more or fewer degrees of freedom than the associated the medical instrument 104. In some embodiments, the input devices may optionally be manual input devices which move with six degrees of freedom, and which may also include an actuatable handle for actuating instruments (for example, for closing grasping jaws, applying an electrical potential to an electrode, delivering a therapeutic treatment, and/or the like).

Figure 1D:
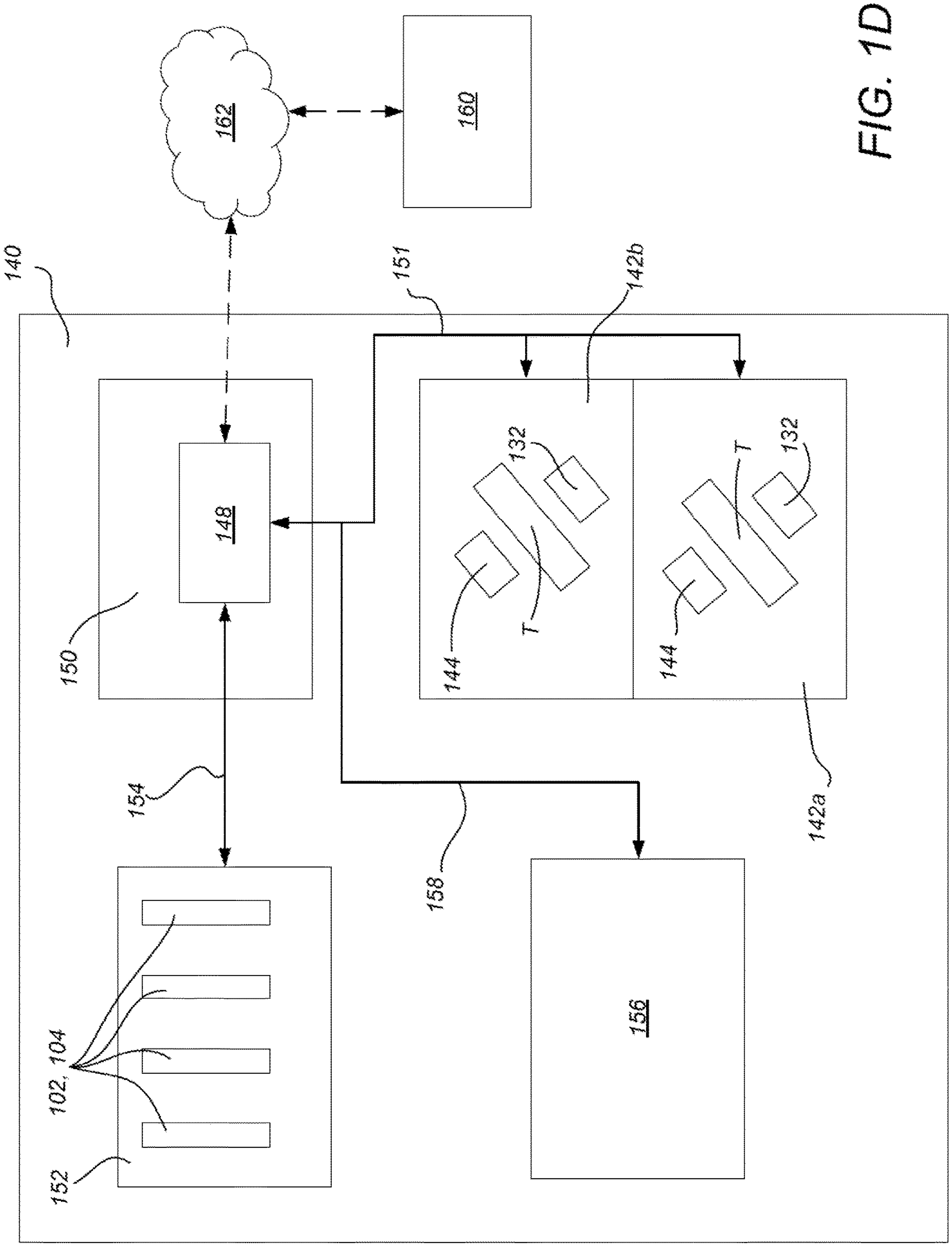
FIG. 1D is a schematic illustration of a care facility configured in accordance with another embodiment of the present technology.

FIG. 1D illustrates an embodiment of a care facility 140 or other operational site configured to host procedures using the various systems described herein. The care facility 140 can include one or more operating rooms 142 (two are shown as operating rooms 142*a-b*) or other facilities for performing procedures using the manipulator assemblies and instruments described herein. One or more tables T (e.g., surgical tables) can be positioned in each of the operating rooms 142*a-b*, and one or more medical devices 144 can be positioned near or at the tables T. The medical devices 144 can include one or more manipulator assemblies (each with one or more manipulator arms), instruments, bases, and other associated components/subcomponents. The medical devices 144 can be teleoperated, remote-controlled, autonomous, semiautonomous, robotic and/or the like. The operating rooms 142*a-b* can include one or more user control systems 132 configured to facilitate user control of the medical devices 144. These user control systems 132 can be the same as or similar to the user control systems 132 described elsewhere in this application with respect to FIG. 1A.

In some embodiments, the care facility 140 includes a management terminal 148 (e.g., a scheduling station or other user interface). The management terminal 148 can be, for example, a personal computer, a mobile device, or some other suitable system. The management terminal 148 can be configured to facilitate scheduling procedures, assigning manipulator assemblies, and/or manipulator arms of those manipulator assemblies, and/or instruments for procedures, managing inventory of procedure components and subcomponents (e.g., the manipulator assemblies, manipulator arms, instruments, etc.), and/or other management functions. In some embodiments, a management terminal 148 is positioned in one, some, or all of the operating rooms 142*a-b*. In some embodiments, the management terminal 148 is positioned in a separate room 150 or area (e.g., a nurses' station, an IT department, or other area). Mobile interfaces (e.g., phones, tablets, laptops, PDAs, etc.) may be configured to allow a user to remotely access the management terminal 148.

The management terminal 148 can be configured to allow a nurse, robotics coordinator, doctor, surgeon, and/or other operator to input a proposed procedure or information related to the procedure. The management terminal 148 can process the information received from the personnel to provide recommended components, rooms, personnel, and/or other parameters for the proposed procedure. In order to provide recommendations, the management terminal 148 can be configured to evaluate schedules (e.g., for rooms, equipment, personnel, etc.), the historical data of devices such as manipulator assemblies or components/subcomponents of such devices (e.g. manipulator arms, etc.), personnel (e.g., which medical persons are) required for the procedure, hardware and fixtures required for the procedures, and/or other data relevant to efficient management of the care facility, its personnel, and the components needed for the procedure. Further details regarding evaluating historical data are described below with respect to FIGS. 3-5B.

The management terminal 148 can be configured to communicate, either wirelessly or via a wired connection, with the one or more operating rooms 142*a-b* and with the personnel associated therewith, as indicated by the arrows 151. For example, the operating rooms 142*a-b* can include terminals and/or mobile devices in communication with the management terminal 148. Facilitating communication between the operating rooms 142*a-b* and the management terminal 148 can allow personnel in the operating rooms 142*a-b* to query the management terminal 148 for information before, during, or after the proposed procedure.

The management terminals 148 of some care facilities 140 are configured to query inventory of various components (e.g., manipulator assemblies 102, manipulator arms, instruments 104, etc.) from a storage room 152 or other area (e.g., an operating room, connected to a robotic/teleoperated system, and/or connected to a manipulator assembly) local to or remote from the care facility 140. Such querying can be performed wirelessly or via a wired connection, as indicated by the arrow 154. Inventory information can include IDs for specific components, historical data for specific components, and/or other relevant information. The individual components may include unique IDs such as, for example, printed and/or adhered labels (e.g., barcodes, QR codes, numeric codes, alphanumeric codes, etc.), digital IDs, light arrays, or other identifying features. In some embodiments, the unique IDs are radio-frequency identification (RFID) tags, near-field communication (NFC) components, Bluetooth® beacons, embedded chips, or other non-visual components.

The management terminal 148 may maintain or otherwise support updatable tables (e.g., spreadsheets). The tables may be automatically updated to account for use of specific components, rooms, etc. In some configurations, a nurse, robotics coordinator, or other personal can manually update the tables.

In some embodiments, the management terminal 148 is in communication with a central sterile services department (CSSD) 156 of the care facility 140, as indicated by the arrow 158. In some cases, the components (e.g., manipulator assemblies, manipulator arms, instruments, etc.) are cleaned and/or tested in the CSSD 156 or in another location (e.g., in situ in an operating room, in a storage area, etc.). Testing may be performed by field service technicians or other operators, or by self-diagnostic functions of the manipulator arms or manipulator assemblies. Test results from the CSSD or otherwise (e.g., performance test data) can be conveyed to the management terminal 148 and the records and historical data for the individual components can be updated. Test results can be conveyed in a number of ways. For example, wear on the components can be rated on a scale of 1-N, with N being a number (e.g., 3, 5, or 10) for the highest wear and 1 being little to no wear. These observed test results can be used to update the historical data of the individual components.

The data processing functionality of the management terminal 148 may be local to the management terminal 148. In some configurations, as illustrated in FIG. 1D, the management terminal 148 can be in communication with a remote server 160 located offsite from the care facility 140. For example, the remote server 160 may be local to the manufacturer of the manipulator assemblies and/or to another entity. The management terminal 148 can be connected to the remote server 160 via a network of distributed servers 162 (e.g., a "cloud") or some other communication protocol. The management terminal(s) 148 can include a control system having one or more processors and a memory. The memory can carry programmed instructions to cause the one or more processors to perform various above-recited functions and operations. In some systems, the above-described functions of the management terminal 148 are performed by the network of distributed servers 162 and/or by the remove server 160, without the need for a centralized management terminal.

The medical devices 100, 100*a*, 100*b*, 144 described herein can include manipulator assemblies 102 that each comprise one or more manipulator arms configured to support medical instruments 104. The manipulator arms may each include kinematic structures comprising any number of joints and links. For example, depending upon the design of the kinematic structure, each of the joints of the kinematic structure may be a non-actuated joint or an actuated joint. In some examples, a non-actuated joint may not include any actuators, or may include only actuator(s) with insufficient motive power to move the associated joint, and therefore is not capable of causing motion of the joint via teleoperation and/or motion control commands from a control system. In some examples, the non-actuated joint may include a brake that permits the control system to prevent and/or restrict motion in the non-actuated joint. In some examples, an actuated joint may include one or more actuators that may control motion of the actuated joint, and may be commanded to move the joint teleoperatively and/or carry out other motion commands. In some examples, an actuated joint may further include a brake. In such examples, the brake may be employed in an actuated joint to hold a current pose of the non-actuated joint rather than to actively control motion of the actuated joint.

Figure 2A:
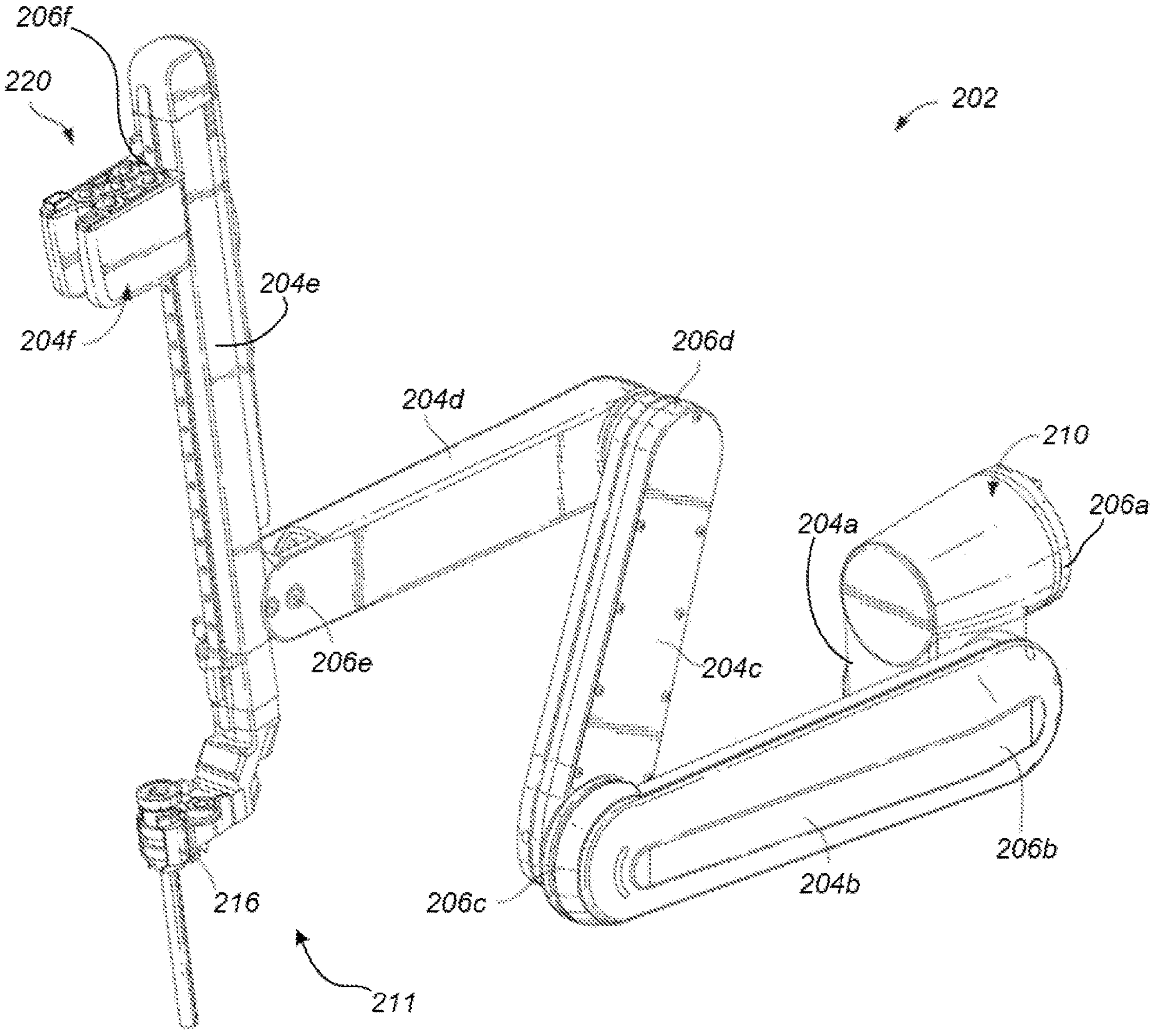
FIG. 2A is an illustration of a manipulator arm configured in accordance with an embodiment of the present technology.

FIG. 2A, for example, illustrates a manipulator arm 202 configured in accordance with embodiments of the present technology. The manipulator arm 202 can share many or all of the functional and structural characteristics of the other manipulator arms (e.g., a manipulator arm of manipulator assembly 102) described herein. As illustrated, the manipulator arm 202 can include a plurality of links 204*a-f* (collectively, "204") connected together and to a proximal structure (not shown) by a plurality of joints 206*a-f* (collectively, "206"). The manipulator arm 202 can be configured to support an instrument (not shown). One or more the joints 206 maybe non-actuated or actuated. In some applications, one or more of the joints 206 are passive and/or configured to resist or prevent unintentional movement of one or more of the links 204 during operation. For example, one or more of the joints 206 can be configured to switch between locked and unlocked configurations.

The manipulator arm 202 can include a mounting structure 210 configured to releasably or fixedly connect the manipulator arm 202 to a mounting site (e.g., a fixed or moveable base, table, ceiling, wall, rollable cart, or any other mounting site described herein). The mounting structure 210 can comprise a joint. For example, in some embodiments, the mounting structure 210 comprises a rotational joint that permits rotational movement of the manipulator arm 202 relative to the mounting site.

One or more of the joints 206 can be rotary joints configured to permit rotation of one link 204 with respect to another link 204 or structure. One or more of the joints 206 can be a prismatic joint configured to permit translation of one link 204 with respect to another link 204 or other structure. Other joint types may also be used to facilitate desired motion of the link 204 and/or of an instrument mounted to the manipulator assembly 102.

The manipulator arm 202 can include an instrument interface 211 configured to releasably receive and connect to one or more instruments. In the example shown in FIG. 2A, the instrument interface 211 is disposed on the links 204*e* and 204*f*, and in other embodiments the instrument interface 211 may be located elsewhere. The instrument interface 211 can include a drive assembly 220 configured to interface with an input assembly of an instrument. In some embodiments, the instrument interface 211 includes one or more alignment features configured to orient an instrument when the instrument is connected to the instrument interface 211. For example, the alignment features can include a groove 216 configured to receive a portion of a shaft of the instrument.

Figure 2B:
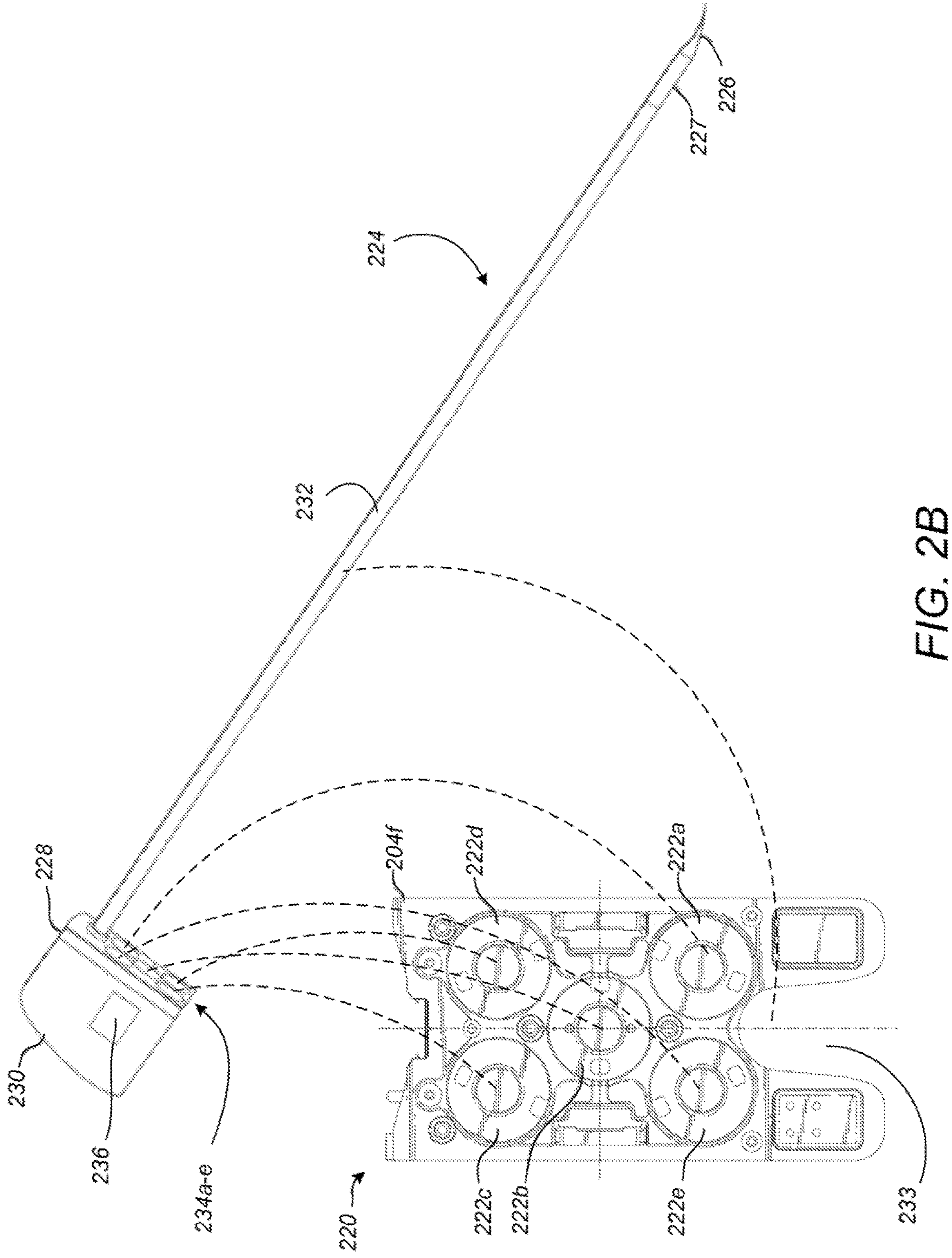
FIG. 2B is an illustration of a drive assembly and an instrument configured for use with of the manipulator assembly of FIG. 2A.

FIG. 2B is an illustration of a portion of the drive assembly 220 and an instrument 224 configured in accordance with embodiments of the present technology. The drive assembly 220 can include one or more drive elements 222 (five are shown as drive elements 222*a-e*). The drive elements 222 can be mounted onto/into the link 204*f* (e.g., a carriage). The drive assembly 220 or some other portion of the manipulator arm 202 can include one or more actuators or motors configured to operate the drive elements 222. In some configurations, each of the separate drive elements 222 is driven by a separate motor/actuator. In other configurations, two or more of the drive elements 222 are driven by a shared motor/actuator. As illustrated in FIG. 2B, the drive elements 222 can be rotary discs or other rotary drive elements. In other embodiments, however, one or more of the drive elements 222 can comprise one or more tabs, protrusions, indentations, or other structures, and be configured to impart any combination of rotary or linear motion onto another structure.

The instrument 224 as shown includes a distal end effector 226, a wrist 227 comprising one or more joints, a proximal end chassis 228, a housing 230 over the chassis 228, and a shaft 232 between the end effector 226 and the chassis 228. In various embodiments, the instrument 224 may have fewer or more than these components, or different instances of these components. For example, in some embodiments, the instrument 224 lacks the wrist 227 or comprises a wrist 227 with different degrees or freedom or range of motion, lacks the chassis 228, and/or lacks the housing 230. As another example, in some embodiments, the chassis 228 and the housing 230 are combined into a single component. The shaft 232 can be configured (e.g., sized and shaped) to fit at least partially within an indentation or channel 233 in the link 204*f*. The end effector 226 is coupled to the shaft 232 with or without one or more intervening joints, such as the wrist 227. Various wrist 227 architectures allow the orientation of the end effector 226 to change with reference to the shaft 232 in various combinations of pitch, yaw, and/or roll. Optionally, the end effector roll function is carried out by rolling the shaft 232 or the chassis 228. Various drivetrain components, subcomponents, and/or other mechanisms are mounted on the chassis 228 and function to receive either mechanical or electrical inputs from the manipulator associated with the instrument 224. These inputs can be used to orient and operate the end effector 226. Example drivetrain components and subcomponents are listed earlier in this application.

Referring to FIG. 2B, the chassis 228 will typically include one or more input elements 234 (five are shown as input elements 234*a-e*) adapted for coupling to drive elements 222 of the manipulator arm 202 (e.g., of the drive assembly of the manipulator arm 202), as indicated by the broken lines connecting respective drive elements 222 to respective input elements 234. Coupling between the drive elements 222 and the input elements 234 can be direct (e.g., with direct contact between the drive elements 222 and the input elements 234) or indirect through one or more intermediate structures. For example, in some applications, an adapter is positioned between the input elements 234 and the drive elements 222. The adapter can include one or more transmission elements (e.g., discs, compliant protrusions or indentations) configured to allow or facilitate the transmission of linear or rotary force (torque), motion, and/or other inputs from the drive elements 222 to the input elements 234. In a medical example, the adapter can be a sterile adapter configured to inhibit or prevent transmission of pathogens from the drive assembly to the instrument 224 (and thereby to a patient). The drive elements 222 drive the input elements 234 on the instrument 224 (or another instrument, such as instrument 104) in response to commands from the control system (e.g., a control system 134, see FIG. 1A). Each of the input elements 234 may be configured to drive/actuate a different movement or action of the instrument 224. For example, a first input element 234*a* may control a first movement parameter (e.g., pitch, yaw, and/or roll about one or more axes) of one or more joints of the instrument 224 (e.g. wrist 227), while a second input element 234*b* controls a second movement parameter. Multiple input elements 234 may be configured to together drive/actuate a coordinated movement/actuation of the instrument 224 (e.g. pitch, yaw, opening or closing jaws, etc.) One or more of the input elements 234 may control an actuation of the end effector such as staple firing, clamp clamping, etc. In some embodiments, one or more of the drive elements 222 of the manipulator arm 202 are configured to be compatible with two or more of the input elements 234. In some embodiments, specific drive elements 222 or subsets of the drive elements 222 are compatible with only a single input element 234 or subset of input elements 234. For example, certain drive elements and input elements may be associated with high-load (e.g., high torque or force) applications, while other drive elements and input elements may only be configured for lower-load applications. In another example, certain drive elements and input elements may be associated with high-speed (e.g., high linear speed or high rotational speed) applications, while other drive elements and input elements may only be configured for lower-speed applications.

Operating parameters of the instrument 224 can be sensed by any number of position, velocity, or acceleration sensors such as encoders, potentiometers, accelerometers, or other sensors to provide sensor data to the device 100 describing the movement of the instrument 224. Other sensors could include torque sensors, current sensors, voltage sensors, and/or temperature sensors. These sensors may be included in the instrument 224, or elsewhere in the system. This sensor data may be used to determine motion of the objects manipulated by the drive elements 222, such as portions of the instrument 224.

As described in more detail in U.S. Pat. No. 6,331,181 (the entire disclosure of which is hereby incorporated by reference in its entirety), the instrument 224 will often include a memory 236, with the memory 236 typically being electrically coupled to a data interface (e.g. as part of the instrument interface 211). This data interface can allow data communication between memory 236 and a computer (e.g., the user control system 132, see FIG. 1A) when the instrument 224 is mounted on the manipulator arm 202 (FIG. 2A).

Instruments (e.g. instrument 104, 224) may differ in size, shape, number of joints, degrees of freedom, function, etc. For example, instruments may have different shaft diameters or end effectors. In some embodiments, the instruments are configured to be coupled to associated drive assemblies, removed from their associated drive assemblies, and be remounted to couple with the same drive assembly or another drive assembly, or be replaced with another instrument. This instrument coupling, removal, and remounting or replacement may occur during a procedure being performed by the medical device, or between procedures performed by the medical device. For a surgical example, a surgical stapler may be used in connection with a given manipulator arm 202 for a first procedure, or for a first portion of the first procedure. Another instrument can be installed on the manipulator arm 202 at another time (e.g. during another procedure or another portion of the first procedure). Additional details are provided in U.S. Pat. No. 8,823,308, the entire disclosure of which is hereby incorporated by reference in its entirety.

In some operational environments, instruments can be combined into combinations with multiple capabilities. Additional details related to these combinations are provided in U.S. Pat. No. 7,725,214 (disclosing "Minimally Invasive Surgical System"), the disclosure of which is incorporated herein by reference in its entirety. Details related to interfaces between the instruments and the manipulator assemblies are provided in U.S. Pat. No. 7,955,322 (disclosing "Wireless Communication in a Robotic Surgical System"), U.S. Pat. No. 8,666,544 (disclosing "Cooperative Minimally Invasive Telesurgical System"), and U.S. Pat. No. 8,529,582 (disclosing "Instrument Interfaces for Robotic Surgical Systems), the disclosures of which are all incorporated herein by reference in their entireties.

Figure 2C:
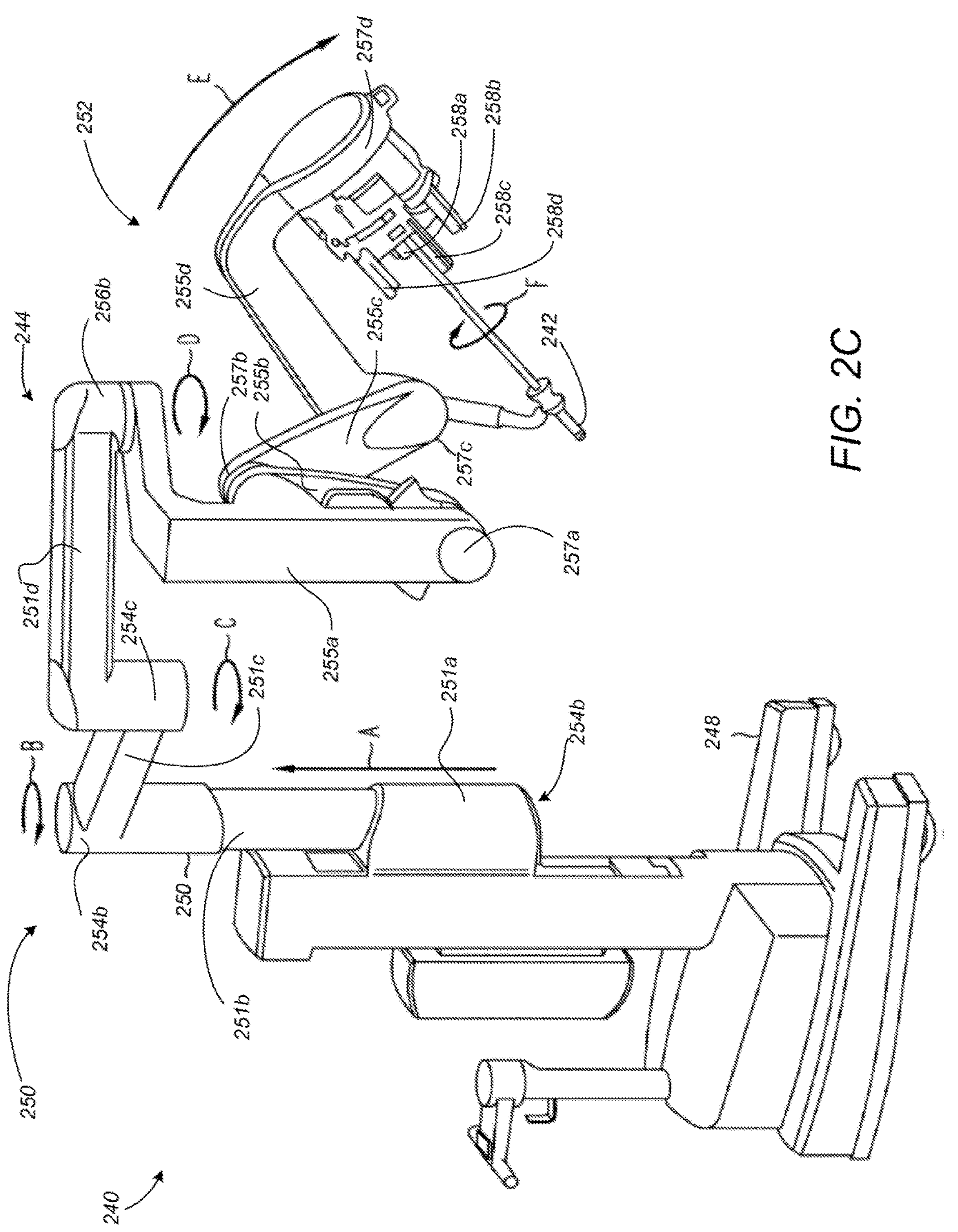
FIG. 2C is an illustration of a manipulator assembly configured in accordance with an embodiment of the present technology.

FIG. 2C illustrates an embodiment of a manipulator assembly 240 that may be used in conjunction with the methods and systems disclosed herein. The manipulator assembly 240 can be, for example, a patient-side cart usable in a robotic system to introduce a plurality of articulated instruments to a work site (e.g., through a single-entry aperture in a patient—the patient is not shown) via an entry guide 242. The aperture may be a minimally invasive incision or a natural body orifice. The entry guide 242 can be a cylindrical structure which is held and manipulated by a manipulator arm 244, which can be mounted on base 248 and can include a setup portion 250 and an entry guide manipulator 252. The setup portion 250 can include a plurality of links 251*a-d* (collectively, "251") and joints 254*a-c* (collectively, "254") which are used to position the entry guide 242 at the aperture. As illustrated, the setup portion 250 can include a prismatic joint 254*a* for adjusting the height of the setup portion 250 (as indicated by arrow "A") and a plurality of rotary joints 254*b-c* for adjusting the horizontal position of the setup portion 250 (as indicated by arrows "B" and "C"). The entry guide manipulator 252 can include a plurality of links 255*a-d* (collectively, "255") and joints 257*a-d* (collectively, "257") used to robotically pivot the entry guide 242 (and the articulated instruments disposed within it at the time) in yaw, pitch and roll angular rotations about the pivot point as indicated by arrows D, E and F, respectively. A plurality of articulated instrument manipulators 258*a-d* (collectively, "258") can be connected to the entry guide manipulator 252.

Figure 2D:
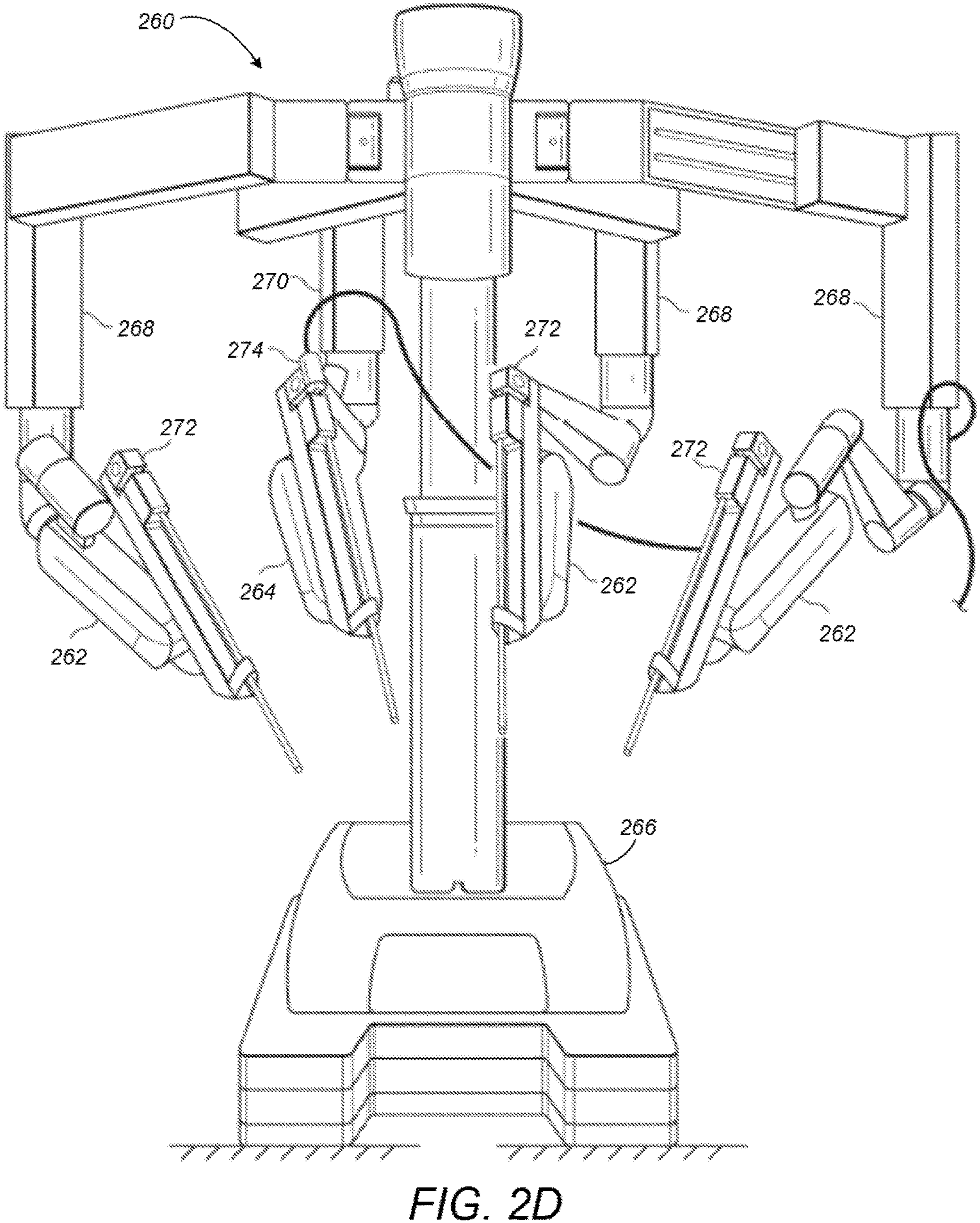
FIG. 2D is an illustration of another manipulator assembly configured in accordance with embodiments of the present technology.

FIG. 2D is a front view that illustrates another manipulator assembly configured in accordance with embodiments of the present technology. Specifically, FIG. 2D illustrates a manipulator assembly 260, which is commercialized as a da Vinci® Surgical System by Intuitive Surgical, Inc. of Sunnyvale, California, U.S.A. In a multi-port telesurgical system, instruments enter the body through two or more separate incisions or natural orifices. In this example, the manipulator assembly 260 includes four manipulator arms 262, 264 supported by a movable unit 266.

The manipulator assembly 260 can include one or more setup structures 268, 270 connected to the base unit 266. The setup structures 268, 270 can be moveably and/or releasably attached to the base unit 266. The one or more manipulator arms 262, 264 can, in some embodiments, be swappable or otherwise replaceable with respect to the individual setup structures 268, 270. Individual instruments 272, 274 may be removably and/or interchangeably mounted to the individual manipulator arms 262, 264. In other embodiments of a manipulator assembly, one or more of the manipulator arms 262, 264 and associated setup structures 268, 270 are individually or in combination mounted on one or more separate movable units (e.g., unit 266) or are fixed to a mechanical ground (e.g., a table, floor, wall, ceiling, etc.) as described herein. It can be seen that various combinations of manipulators and their associated support structures may be used.

As described above, increased use of the components or subcomponents of manipulator assemblies or instruments, as compared to that of other manipulator assemblies or instruments, can result in greater loading, use, or wear for those components or subcomponents. Certain embodiments of the present technology are configured to reduce such greater loading or wear. In various embodiments, use is allocated to the manipulator assemblies, or the components of subcomponents of manipulator assemblies (e.g., manipulator arms, drivetrains, etc.) in a random or pseudorandom manner, in a sequential order, based on historical data, or in a manner combining the foregoing. Examples of historical data include test data (e.g. performance test data), usage data (e.g. prior use history), and the like. Historical data associated with a manipulator assembly can be data of a manipulator arm, a joint, a link, a drive element, a drive assembly, a subcomponent of the drive assembly coupled to any drive element of the plurality of drive elements (e.g. transmission elements, actuators, etc.), and/or other related structures involved in the physical operation of the manipulator assembly. As a specific example, usage or test data associated with of the manipulator assembly can comprise usage or test data of a manipulator assembly, a component or subcomponent of the manipulator assembly, etc. These aspects are discussed in more detail here and further below.

As a specific example, certain embodiments of the present technology are configured to monitor specific loading, usage, or wear on the components and subcomponents of a device in order to estimate, empirically measure, or otherwise account for different types of loading, wear, or use on the components and subcomponents. Use/load monitoring can be performed manually, automatically, or with a combination of manual and automatic systems. Such systems and methods will now be described in a teleoperation context with respect to the medical device 100 illustrated in FIGS. 1A and 1D. The techniques described in the teleoperation context can also be applied to non-teleoperated contexts and non-teleoperated components.

Referring back to FIG. 1A, for a given procedure, one or more specific instruments 104 are coupled to the one or more specific manipulator assemblies 102. These instruments may include medical instruments such as manipulation instruments (e.g., graspers, hooks, staplers, etc.) and imaging instruments (e.g., optical or infrared cameras, ultrasonic sensors, etc.), and/or other appropriate instruments for the given procedure. The specific manipulator assemblies 102, their respective connection points, poses, shapes, positions, model numbers, etc. can be recorded and archived. Additionally, the couplings between instruments 104 and manipulator assemblies 102, the details of the coupling between the instruments 104 and the manipulator assemblies 102 can be identified in any appropriate manner and recorded. For example, the operator O or other person can manually enter the couplings before or after the procedure. In some configurations, the manipulator assemblies 102 and/or the instruments 104 include structures configured to automatically identify the couplings between components. For example, either or both of the instruments 104 and manipulator assemblies 102 can include radio-frequency identification (RFID) tags, near-field communication (NFC) components, Bluetooth® beacons, embedded chips, optical UPC or QR codes, magnets providing unique magnetic signatures, or other components configured to identify and/or detect the type of instrument 104 coupled to a given manipulator assembly 102. The above-listed components can also be configured to help identify couplings between specific drive elements of the manipulator assemblies 102 with specific input elements of the instruments 104. The identified couplings of the instruments 104 and the manipulator assemblies 102 can be recorded locally or in a remote database. For example, the control system 134 and/or the user control system 132 can include memory configured to receive and store identified couplings.

The recorded data reflecting pairings between specific instruments 104 and specific manipulator assemblies 102 and/or pairings between specific drive elements and specific input elements) can be usage data comprising a part of the overall historical data. The overall historical data can include the type of instrument 104 coupled to a manipulator arm of a manipulator assembly 102, the date and/or duration of use of the instrument 104 with that manipulator arm, the installation position of the manipulator assembly 102, the pose of manipulator arm(s) of the manipulator assembly 102, the number and/or types of actuations of components or subcomponents (e.g. of specific manipulator arms, of the specific drive or other elements), the load or estimated wear borne by the manipulator arm(s), the operating conditions, any of the previously listed parameters affecting load, use, or wear, and/or other information associated with the couplings and uses of the portions or the entirety of the manipulator assemblies. The number/types of actuation data associated with the manipulator assemblies or their components or subcomponents (e.g. manipulator arms or drive elements) can include number and/or frequency of direction reversals (e.g., rotations/translations of the drive elements in different directions), forces realized (e.g., aggregate and/or peak values), torques realized (e.g., aggregate and/or peak values), speed of movement realized, the degree of freedom associated with previously paired instruments/input elements, the identity of a user of the manipulator assembly, and/or magnitude of overall motion. The above-described data can be recorded and associated with manipulator assemblies. The poses, duration of use, number of uses, types of procedure, and other information pertaining to the specific manipulator assemblies during use can be included in usage data comprising the historical data. In some embodiments, environmental conditions are also associated with the recorded usage data. These environmental conditions can include temperature, humidity, altitude, etc. As discussed earlier, historical data can also include other data about the manipulator assemblies, such as test data or performance data.

The recorded historical data can be compiled and/or processed by a server. The server can be local (e.g., associated with the control system 134, the user control system 132, and/or be on hardware or software component located at the facility in which the manipulator assemblies are located). In some configurations, such as that shown in FIG. 1D, the server is remote or otherwise offsite from the medical device 100. For example, the server can be part of a distributed network of servers (e.g., a "cloud" network) or part of backend hardware located at a manufacturer or service provider facility. Additional details about suitable servers associated with the present technology are provided below with reference to FIG. 3.

Various metrics or other proxies of historical use (e.g. loading) or wear can be calculated based on the recorded historical data and associated with the specific manipulator assemblies 102 (or of specific manipulator arms comprising the specific manipulator assemblies, drive elements of those manipulator assemblies) or instruments 104 (or input elements of manipulator assemblies). In some configurations, a binary metric is used. For example, in an embodiment, pairing with a high-load instrument (e.g., a surgical stapler) or with a high-load input element garners a "1" while pairing with a low-load instrument (or with a low-load input element) is recorded as a "0" value. Binary scoring could also be associated with the specific type of instrument 104 or input element. For example, a specific instrument 104 or input element can be associated with a "1", and a manipulator assembly 102 or manipulator arm or drive element (or other part of the drive assembly comprising the drive element) can be given a "1" each time the manipulator assembly 102 is paired and used with that instrument 104/input element, or that drive element is paired and used with that input element. Scoring can also account for the type of pose, position, and/or other operating parameter of the specific manipulator assemblies 102 or manipulator arms. For example, certain poses can be assigned a first score, while other poses can be assigned a second, different score.

The metrics for historical loading, use, or wear can comprise, in some applications, aggregations, summations, or other combinations of all or a subset of the above-recited historical data. For example, total actuations, total time spent in use (e.g., with a specific type of instrument or input element), total number of direction changes/reversals, or other operational parameter etc. can be associated with a given manipulator assembly 102 and/or with one or more of the manipulator arms, drive assemblies, or drive elements. As a specific example, a metric can comprise a combination of the type of instrument 104 (or the input element) coupled with a manipulator arm (or coupled to a drive element), along with the total time of the coupling. As a further example, the linear or rotary forces experienced by the manipulator arm (or by the drive element or another part of the drive assembly) can also be used in the combination. As another example, in some configurations, the number of direction reversals experienced by the manipulator arms (or by the drive elements (or of the drive assemblies comprising the drive elements) can also be used in the combination, such as in addition to or instead of the number of revolutions and/or translations. Additional operating parameters may be used to formulate aggregated metrics. For example, in some configurations, numbers and/or aggregate total degrees of revolution of one or more joints can be used to formulate aggregated metrics.

In some embodiments, the manipulator assemblies 102, or manipulator arms comprising the manipulator assemblies 102, or the drive elements (or other parts of the drive assemblies comprising the drive elements), can be tested for performance, or for specific wear. This testing could be performed onsite (e.g., in a CSSD, such as CSSD 156 of FIG. 1D) or at separate testing facility. The test data observed during such tests can be combined with the historical data and used as appropriate in determinations of metrics for loading, wear, use, etc. For example, the test data can supplement calculation of an overall aggregated metric for the specific manipulator assemblies 102, manipulator arms, drive elements, etc. For example, an observed wear measurement of a joint can be used in determining an aggregated metric associated with the manipulator arm having that joint. In some applications, such observed wear is assigned a value between "1" and "N," with N being a number greater than one. For example, N could be 2. In this case, each manipulator assembly 102, manipulator arm, or drive element, etc. can be assigned a value between 1 (low or no observed wear) and 2 (high wear).

The empirical/observed loading, use, or wear can be associated with specific types of loading, use, or wear and used to supplement metrics that implicate those types of loading, use, or wear. For example, observed loading, use, or wear on certain gears or bearings may be associated with specific types of loading, use, or wear (e.g., number of direction reversals, magnitude of load, etc.). This specific observed loading, use, or wear can be assigned a value that is used in calculations of the actual metrics. For example, observed loading, use, or wear associated with a number of direction reversals can be added to, multiplied by, or otherwise combined with previously recorded metrics associated with direction reversals. Such associations can be made with respect to some or all of the other above-described quantified features.

The observed wear can be input to a user interface (UI) on one of the control systems (e.g., control systems 132 in FIGS. 1A and 1D, control system 134 in FIG. 1A). In some configurations, the observed wear can be input into another UI on, for example, a handheld device, a terminal in a location other than the room in which the medical device is located, or some other UI. For example, a test facility may include one or more handheld devices or terminals having UIs for inputting observed wear characteristics (e.g., visually observable wear) associated with specific components and/or subcomponents of the manipulator assembly or other part of the device. Data input into the above-described UIs can be sent via a wired connection, wireless connection, or other connection to the above-described server for storage and analysis. Data from tests (e.g., performance or wear tests) can be automatically compiled and sent to the above-described server. The data from the tests can be combined with other historical data to provide a more holistic metric for one or more component/subcomponent. In some configurations, data from wear tests instead of data from observed wear are compiled.

The above-described metrics and data can be associated with specific manipulator assemblies 102, manipulator arms, or drive elements (or other elements of the drive assemblies associated with the drive elements) over the life of that structure. For example, specific manipulator assemblies, manipulator arms, joints, links, and specific drive elements (and/or other elements of the drive assemblies associated with the drive elements) can be assigned unique identifiers. In some embodiments, each component and subcomponent has an identifier unique to the structure that is attached to (e.g. to a specific manipulator arm of the manipulator assembly 102), but is not necessarily universally unique. The historical data and/or determined metrics can be associated with these unique identifiers, allowing a user to recall metrics for manipulator assemblies 102 and/or specific drive elements available for use with a given procedure.

Recorded usage data is a type of historical data and can be updated in response to additional data obtained in subsequent procedures just like other types of historical data can be updated (e.g. recorded test data can be augmented by additional test data). The historical data (e.g. usage data, test data, etc.) can be managed by a control system (e.g., the below-described management systems) or other automated system. Assignment recommendations for specific instrument-manipulator pairings, manipulator arm or manipulator assembly locations, and/or other operating configurations can be generated by the control system. The control system can convey the recommendation to a user. In some embodiments, the historical data (usage data, test data, etc.) can be presented to a user as single values in multiple categories (e.g., total use with a certain type of instrument, total wear estimation for a joint/link, total time used, etc.). In some applications, the historical data (e.g. usage data, test data, etc.) can be presented as a vector, matrix, table, graph, or other format indicating metric values and other data over the course of time (e.g., over hours, days, months, years, etc.). In some instances, the historical data (e.g. usage data, test data, etc.) of the manipulator assemblies and/or components or subcomponents thereof are retained after maintenance or repair. In other instances, such historical data is totally or partially erased or reset after maintenance or repair, such as based on the type and result of the maintenance or repair. In applications where historical data includes values over time (e.g., over hours, days, months, years, etc.), the erasure or resets may be noted in the history.

Historical data associated with specific procedures, instruments, operators, etc. can be used to forecast wear expected for future procedures. These future procedures can include procedures due in the coming hours, days, weeks, months, years, etc. For example, in a manipulator assembly including a plurality of manipulator arms, specific manipulator arms may be used in every procedure, other manipulator arms used in only a subset of procedures, and still other manipulator arms (e.g., manipulator arms at specific locations on the manipulator assembly) may never be used. Historical data gathered for this manipulator system may be used to predict the future wear on the manipulators arms (and/or components/subcomponents thereof) based on the location of the manipulator arms on the manipulator assembly. As discussed more generally below, a schedule for manipulator arm position on the manipulator assembly can be generated to more evenly distribute loading or wear on the manipulator arms or to reduce the risk that a manipulator arm provides lower performance, or fails substantially earlier, than another manipulator arm.

Figure 3:
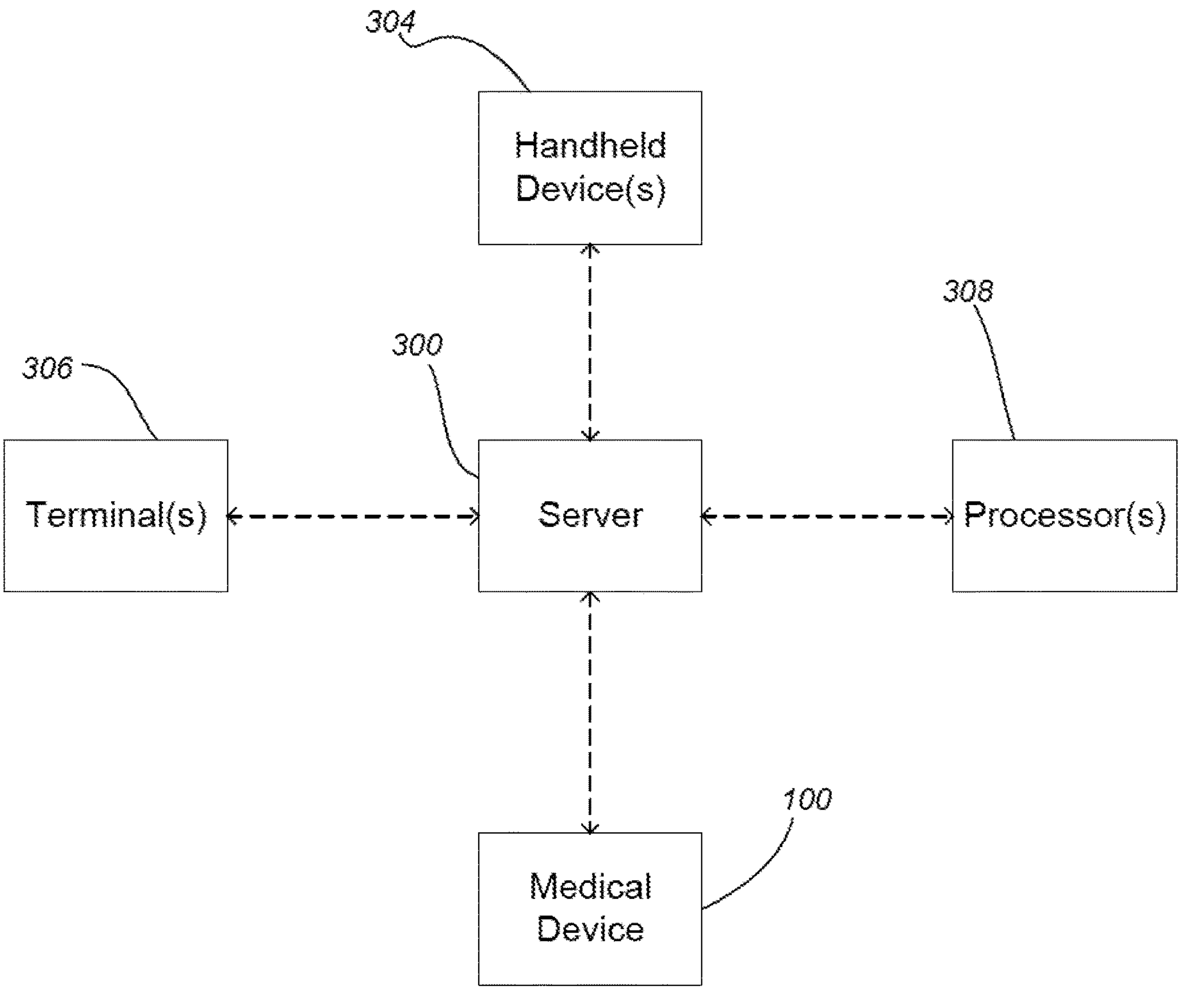
FIG. 3 is a schematic illustration of a system for managing devices in accordance with embodiments of the present technology.

As illustrated in FIG. 3, the historical data and associated data can be maintained and stored on a server 300. This server can be the same, above-described server or some other server. One of skill in the art will appreciate that specific hardware and software features may be added and/or omitted to accommodate the above-described collections and other functions. As indicated by the broken arrows, the server 300 can be operably connected to one or more other components or systems. The components can include the medical device 100, one or more handheld devices 304, one or more terminals 306, and/or one or more local (to the server) or remote processors 308 (collectively, data components). As described above, the server 300 may be local to or physically integral with any of the other data components. Data from each of the data components may be communicated over a wired connection, a wireless connection, and/or via cloud server. Each of the data components may be configured to access information from the server 300. Preferably, such access is limited to the data associated with specific manipulator assemblies 102, manipulator arms, and/or drive elements owned or operated by the entity requesting information from the server 300.

Although FIGS. 4A, 4B, 5A, 5B are discussed below generally in conjunction with manipulator arms, the methods and techniques described can also be applied to manipulator assemblies and other components or subcomponents.

Figure 4A:
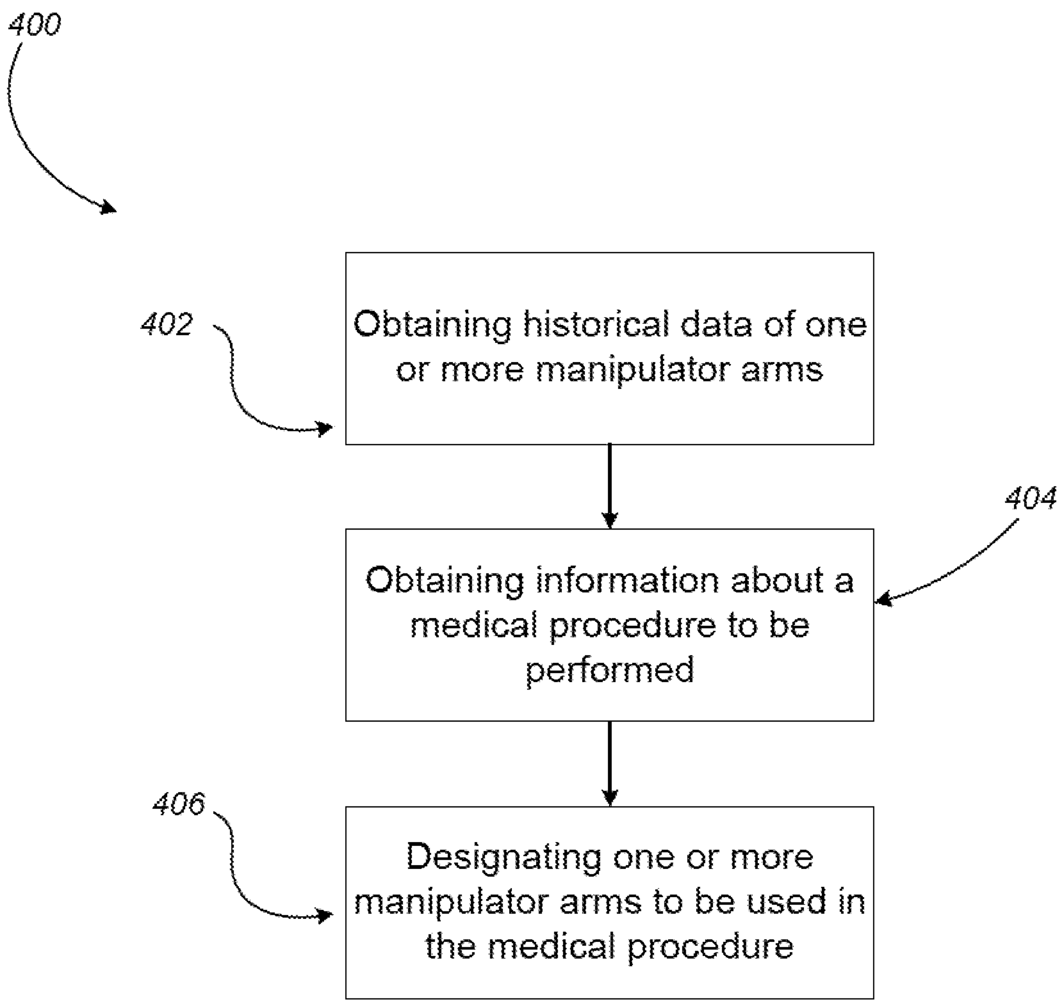
FIG. 4A is a schematic illustration of a method of designating manipulator arms for use in a medical procedure.

FIG. 4A illustrates a method 400 of designating manipulator arms for use in a medical procedure in accordance with embodiments of the present technology. The method 400 can be performed, for example, by one or more processors of a control system executing programmed instructions of a memory of the control system. The method 400 can include obtaining historical data of a plurality of manipulator arms (block 402). The historical data can include data selected from the group consisting of usage data and test data. The method 400 can include obtaining information about a medical procedure to be performed (block 404) and designating (e.g., based on the historical data and the information about the medical procedure) one or more manipulator arms of the plurality of manipulator arms to be used in the medical procedure (block 406).

Figure 4B:
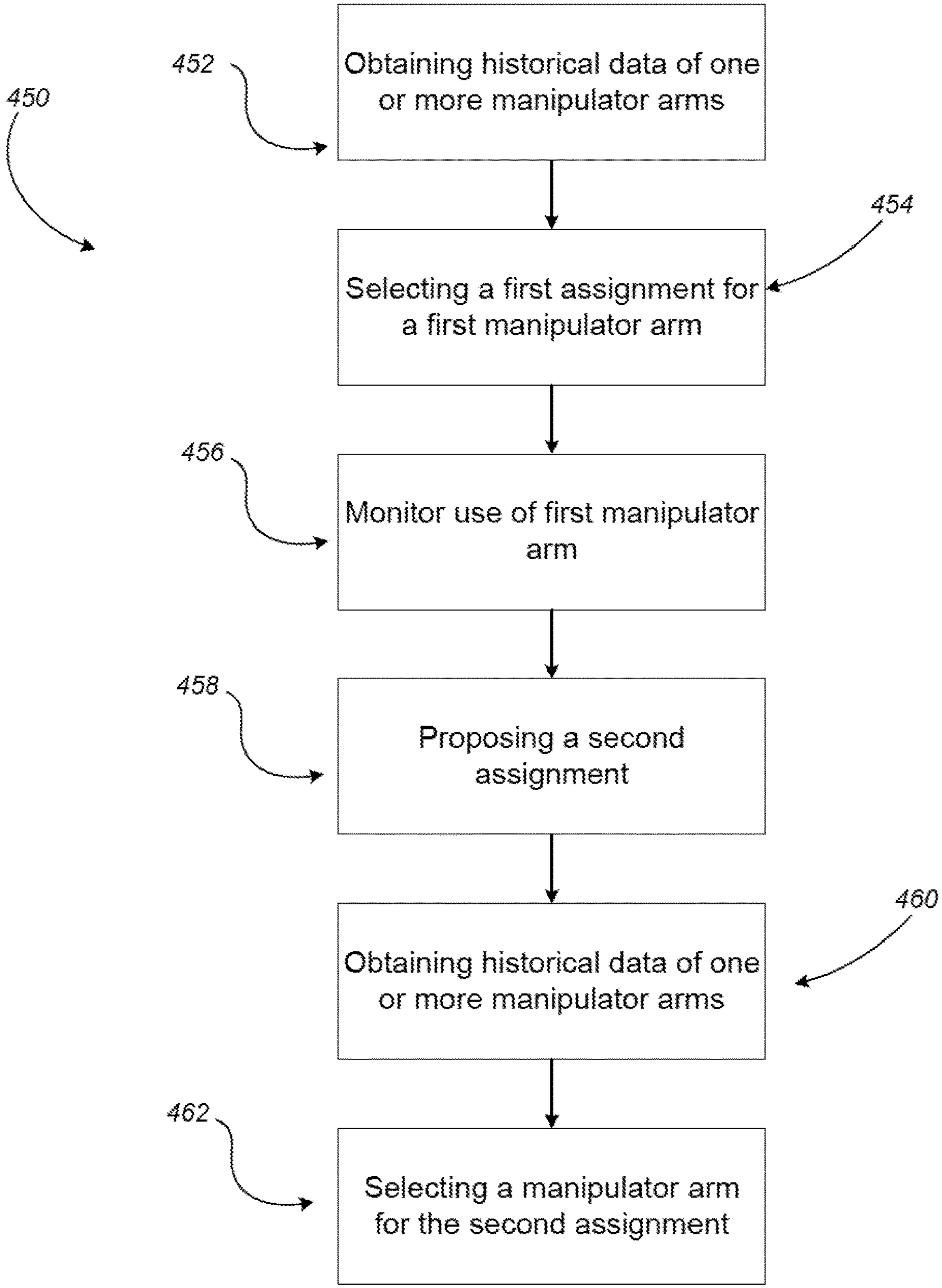
FIG. 4B is a schematic illustration of a method of selecting assignments for manipulator arms in a medical device configured in accordance with embodiments of the present technology.

FIG. 4B illustrates a method 450 of selecting assignments for manipulator arms in a medical device configured in accordance with embodiments of the present technology. In some configurations, the selections described in connection with the method 450 of FIG. 4B are made in order to spread or balance loading, usage, or wear on manipulator arms, manipulator arms, and/or on other components/subcomponents of a medical device. The method 450 can include obtaining historical data of one or more manipulator arms considered for a first assignment of a plurality of assignments (block 452). The historical data can include, for example, usage data and/or test data. Usage data can include data recorded or otherwise gathered during previous use (if any) of the manipulator arms in previous assignments. Test data can include observed and/or measured wear and condition of the manipulator arms (e.g., data obtained from tests and/or cleaning performed in a CSSD).

The plurality of assignments can be determined by obtaining information about the instrument types to be used for the assignments and/or the type of procedure (e.g., a medical procedure) to be performed during such assignments. The method 450 can include selecting the first assignment (e.g., a first match with a first instrument type, a first pose/shape/position with respect to a patient, a location of the first manipulator arm, and/or some other operating parameter) for a first manipulator arm (block 454) and causing the first manipulator arm to adopt the first assignment. Selection of the first assignment can be conveyed to a user of the system via instructions (e.g., instructions for the pose, shape, instrument pairing, or other parameter of the first manipulator arm). Selection of the first manipulator arm can be based, at least in part, on the suitability of functional characteristics of the first manipulator arm for the first assignment as compared to other manipulator arms. For example, the first assignment may require a high-load application for which only a subset of the manipulator arms is suitable or may require use with a type of instrument with which only a subset of the manipulator arms is configured to be coupled. In some embodiments, the first assignment requires use in a type of procedure for which only a subset of the manipulator arms is usable. The requirements of the first assignment (e.g., the type of instrument, type of procedure, attachment position, shape, pose, etc.) can be determined based on one or more of the following: a stage of a procedure; a number of uses of the manipulator arms; a previous instrument previously coupled with the manipulator arms; previous instrument degrees of freedom driven by the manipulator arms; and an identity of the user of the device. In some embodiments, causing the manipulator arm to adopt the first assignment includes commanding personnel to configure the first manipulator in accordance with the first assignment. In some embodiments, configuring the first manipulator arm is performed automatically by a component of the system. For example, the first manipulator arm may be moved automatically into the pose, shape, and/or other characteristic of the first assignment.

The first assignment can be available to two or more of the manipulator arms. The first assignment, for example, may be selected from a plurality of available assignments (e.g., in a random or pseudorandom manner). In some embodiments, the first assignment is selected from a list of assignments arranged in sequential order. In other embodiments, the first assignment is selected based on determining an amount of previous use of the first manipulator arm.

The method 450 can include monitoring, tracking, and/or recording the use of the first manipulator arm during the first assignment (block 456). Tracked statistics can include, for example, number of uses of the drive elements of the manipulator arm, identification of the instrument driven by the manipulator arm, degrees of freedom driven by the drive elements, duration of use, loads realized during use, pose of the manipulator arm, shape of the manipulator arm, type of procedure for which the manipulator arm was used, amount of use of individual joints of the manipulator arm (e.g., ranges and/or total aggregate amount of rotation/translation of the joints), and/or any other useful information.

The method 450 can include proposing a second assignment for a manipulator arm (block 458). Historical data for one or more manipulator assemblies (e.g., of one or more manipulator arms or other parts for these one or more manipulator assemblies) can be obtained to aid in the selection of a manipulator arm for the second assignment (block 460). The manipulator arms considered for the second assignment can include the first manipulator arm selected for the first assignment. In some instances, the second assignment is proposed during the performance of the first operation. In some instances, the second assignment is proposed after the completion of the first assignment. In still other instances, the second assignment is proposed concurrently with proposal of the first assignment. The second assignment can designate operating parameters of a manipulator arm in the same or a similar way in which the first assignment designates the operating parameters of the first manipulator arm.

A manipulator arm can be selected for the second assignment (block 462) based on, for example, an evaluation of historical data (e.g., usage data) of a plurality of drive elements. The historical data includes the same or similar data to that described above with respect to block 452. In some embodiments, the historical data obtained and analyzed for the second assignment is updated with historical data recorded during the first assignment. Selection of a manipulator arm of the second assignment can be based, for example, on determining a manipulator arm that has been less used for the parameters required for the second assignment. In some configurations, the second assignment is assigned to a second manipulator arm during a time overlapping with when the first manipulator arm has adopted or is adopting the first assignment. In some embodiments, the second assignment is assigned to the first manipulator arm (e.g., based on further usage information/data) and the first manipulator arm is transitioned from the first assignment to the second assignment.

The first and second assignments can be assigned to first and second manipulator arms, respectively, such that the less used of the two manipulator arms is paired with a more demanding of the first and second assignments. The less used manipulator arm can be, for example, the manipulator arm with a lower amount of use as measured by a use metric (e.g., duration of use, magnitude of experienced forces, etc.), a lower wear amount, and/or other parameters. In some embodiments, the less used manipulator arm is determined based on at least one of the following: a duration of use of the manipulator arms a number of uses of the manipulator arms; a wear amount of the manipulator arms; previous procedures performed by the manipulator arms; previous instruments driven by the manipulator arms; and an amount of use of a joint of the manipulator arms. In some embodiments, the method can include tracking usage of the manipulator arm used in the second assignment and recording the usage data as historical data. The method can include designating (e.g., based on the historical data and/or the information about the procedure) one or more manipulator arms of a plurality of manipulator arms not to be used in the procedure.

Figure 5A:
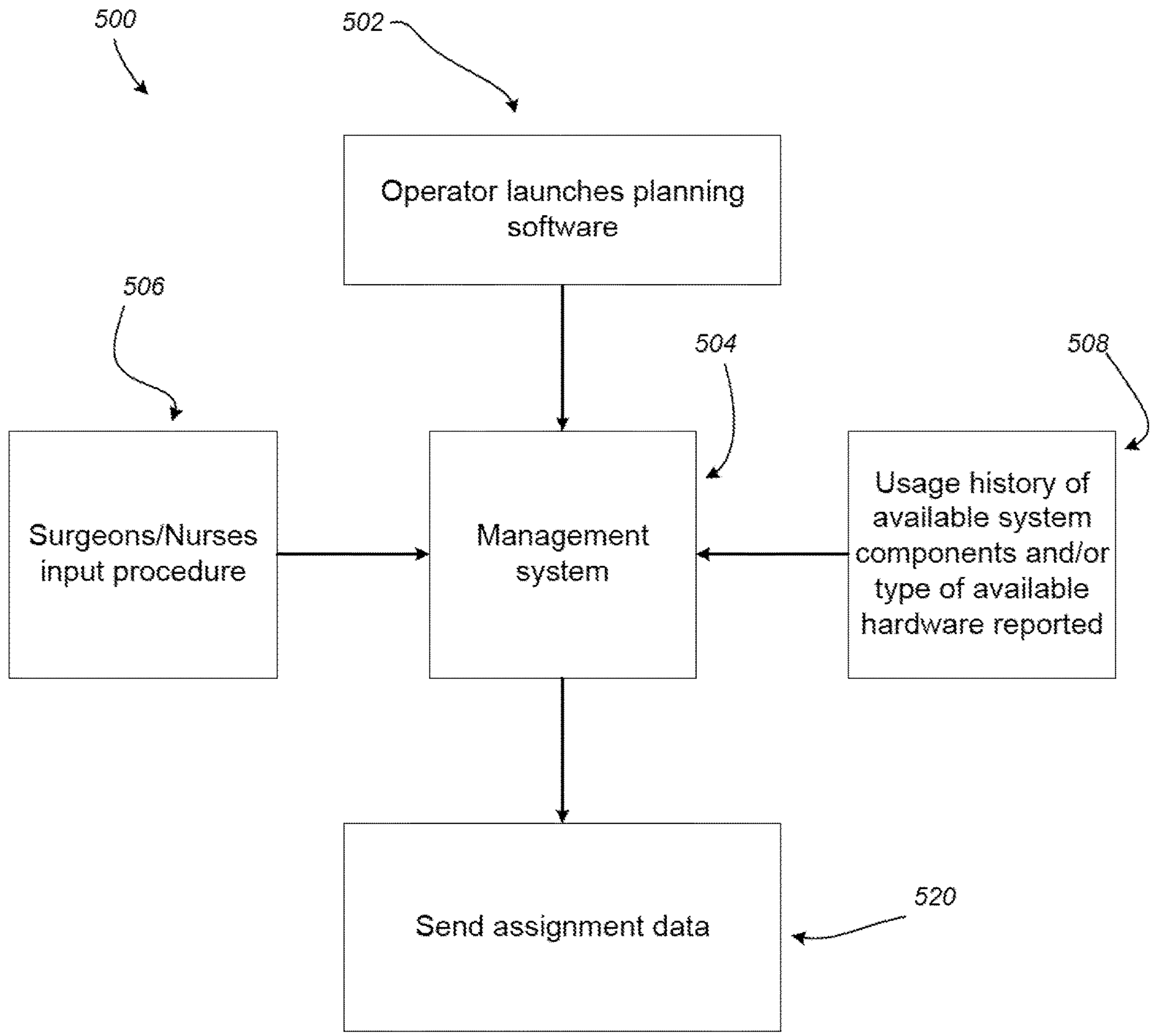
FIG. 5A is a schematic illustration of a method of managing devices in in accordance with embodiments of the present technology.
Figure 5B:
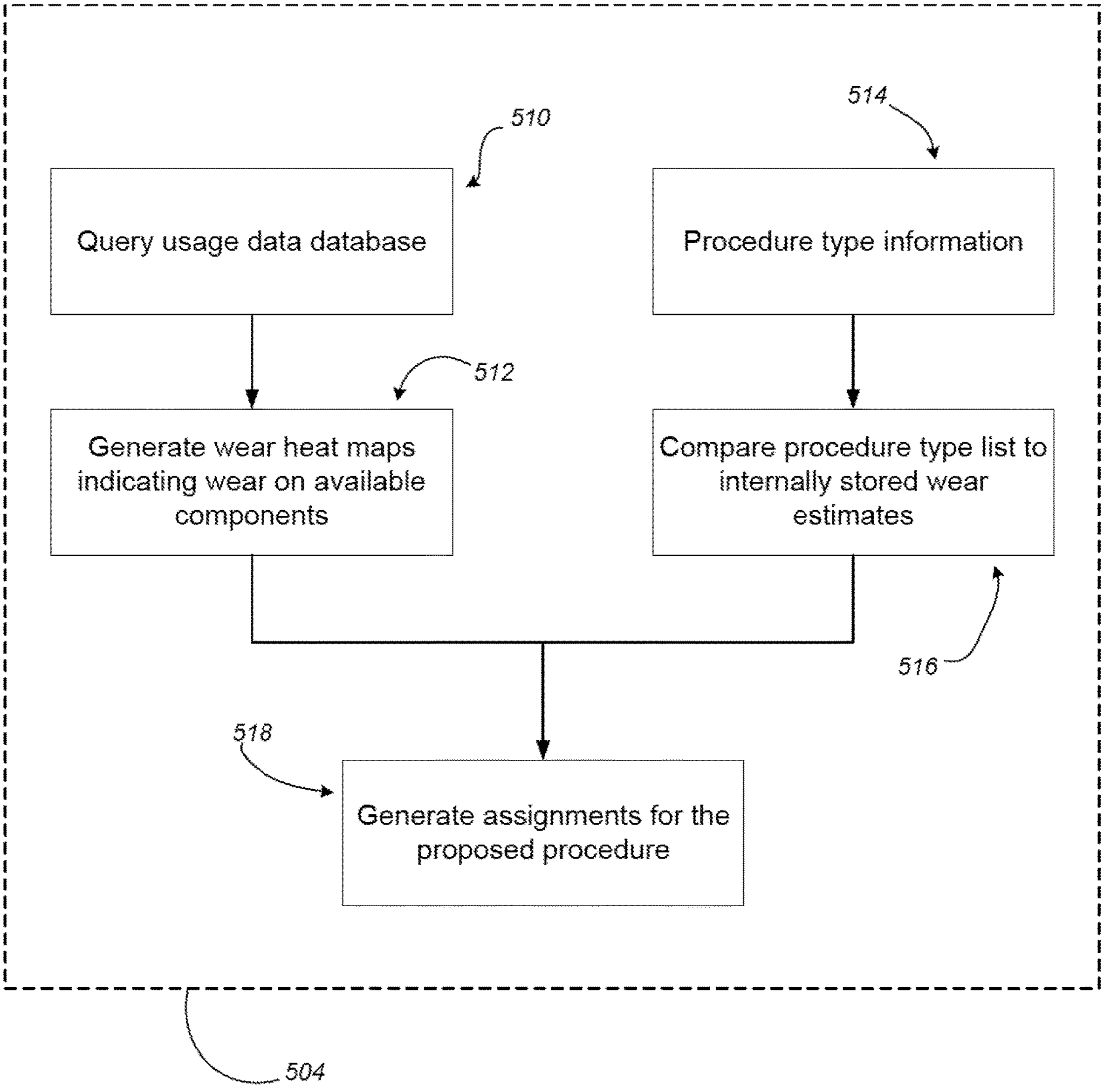
FIG. 5B is a schematic illustration of the wear-balancing agent of FIG. 4A.

FIGS. 5A and 5B illustrate an example method 500 of managing devices in accordance with embodiments of the present technology. The method 500 can be used for balancing or spreading the loading, use, or wear for components and/or subcomponents of manipulator assemblies. As illustrated at block 502, for a given procedure, an operator can launch planning software associated with setting up a medical device for a given procedure. A management system 504 may be notified of the software launch. The management system 504 can be, for example, a control system having at least one processor and a memory. In some embodiments, the management system 504 comprises software associated with the above-described management terminal 148. The management system 504 can include instructions configured to cause the at least one processor to perform various below-described operations and/or the above-described methods of FIGS. 4A-4B. The management system 504 can be maintained, for example, on the above described-server 300 or some other data-processing hub configured to manage data and instructions associated with spreading wear on the medical device. The management system 504 may be maintained and/or operated local to the medical device (e.g., in the same room or at the same facility). In some embodiments, the management system 504 is maintained and/or operated at a location remote to the medical device.

At block 506, an operator can input (e.g., via one of the above-described UIs) the upcoming procedure. For a medical example, a type of surgery or other procedure may be input. In some applications, the required instruments and/or estimated time of use of specific instruments may be input. For example, the estimated time of use can be based at least in part on observed times of use in previous procedures of the same type. In some embodiments, the required location, pose, orientation, and/or shape of a manipulator arm can be input. This information may be conveyed to the management system 504. In some configurations, a scheduling system (e.g., a hospital's scheduling system) can automatically input information about upcoming procedures.

Referring to block 508, the usage histories of the various available components (e.g., manipulator assembly 102, manipulator arm 202 and/or drive elements 222 in FIGS. 1A and 2B) may be reported to the management system 504. In some embodiments, the available overall system architecture (e.g., mounting structures, type of surgical table, etc.) may also be reported. The usage histories may be reported from the above-described server 300 or from some other local or remote database.

Further details of the functions performed by the management system 504 are explained with reference to FIG. 5B. As indicated in block 510, the management system 504 can, in some configurations, query the usage history information (e.g., the information provided in block 508 of FIG. 5A) to generate a heat map (block 512) indicating wear on the available components. This heat map can indicate the above-described usage metrics and usage histories of various available components. For example, aggregated totals from previous binary metrics could be reflected for each component and/or subcomponent could be reflected in a heat map of the available inventory.

Before, after, or contemporaneous with performing the operations in blocks 510 and 512, the procedure type information can be analyzed (block 514). The procedure type information can include the required instruments, manipulator poses, usage durations, and other procedure-specific information. In some embodiments, the procedure type information is pulled from a database. In some embodiments, the surgeon, nurse, or other person, inputs the procedure type information (e.g., as indicated in block 506 of FIG. 5A). The functions performed by the management system can include comparing the input procedure type wear estimates associated with the procedure (block 516). The wear estimates can be calculated using usage information associated with the type of procedure (e.g., the type of instruments, durations of use, and other information). Wear estimates associated with various procedures may be manually calculated. In some embodiment wear estimates are generated based on empirical data from past similar or identical procedures. For example, for a gall bladder removal, wear estimates may be generated based on previously performed gall bladder removal procedures, and the actual recorded data gathered from these past procedures. Wear estimates may be updated and stored on a server operated by a care provider (e.g., a hospital, hospital network, or other care provider) and/or on a server maintained by a manufacturer or other service provider separate from the care provider.

Given the data gathered and analyzed in blocks 510-516, the management system can generate assignments for the proposed procedure (block 518). The assignments can include which manipulator arms are to be used with which instruments, position/pose/shape of one or more manipulator arms, and/or other operating parameters. Determining the appropriate assignments can include comparing different manipulator arms and/or individual drive elements and their respective usage histories, recorded data, observed data, and/or other metrics. In some instances, a "less used" manipulator assembly, manipulator arm, or drive element can be selected from the available inventory. The less used manipulator assembly, manipulator arm, or drive element can be the one that is (1) overall appropriate for the proposed procedure (e.g., it is high-load if high-load operations are required) and has (2) an overall aggregated metric or usage history for the proposed procedure that indicates that has been used less for the procedure than some or all of the other available manipulator arms and/or drive elements. The scores/usage history can be queried with respect to overall aggregate metric value or by a metric value in specific subcategories (e.g., types of wear). Determining and assigning a less used component can help to distribute wear more evenly through the inventory of a given care provider to prolong the overall life of the manipulator arms.

In some implementations, the management system 504 can be configured to assign manipulator assemblies, manipulator arms, and/or drive elements based on a predetermined schedule over the course of multiple assignments. For example, the manipulator assemblies/manipulator arms/drive elements may be assigned a schedule that is arranged to spread or balance usage, load, and/or wear on that manipulator assembly/manipulator arm/drive element as the manipulator assembly/manipulator arm/drive element is reused in subsequent assignments. The schedule can include an order in which types of instruments should be used with a specific manipulator arm and/or an order in which a specific manipulator assembly or manipulator arm is to be used for specific operating parameters (e.g., type of procedure, shape, pose, or other operating parameter). Following predetermined schedules in this matter can help to ensure that each manipulator assembly/manipulator arm/drive element is loaded or worn more evenly that would be the case without a schedule.

These recommended assignments can be communicated (block 520—also illustrated in FIG. 5A) via a software interface or other suitable component (e.g., via the management terminal(s) 148 described above with respect to FIG. 1D). For example, the interface could comprise a mechanical constraint that impedes or prohibits the operator from connecting an instrument to a manipulator arm specifically assigned. In some embodiments, the interface could comprise a sensor that provides an indication of instrument orientation or position, and the system can provide an indication (e.g., audible, visible, and/or tactile feedback such as alarm message, sound, or vibrations) configured to alert a user if an instrument is not connected to the correct manipulator arm. Similar interfaces, sensors, and indications can be used to ensure manipulator arms are disposed at the correct location, in the correct poses, and/or in the correct orientations. In some embodiments, the assignments are communicated to an operator. The communication can occur prior to a procedure, during a break in a procedure, and/or between a first procedure and a second procedure. The recommended assignments can include assignments to use specific manipulator assemblies (or manipulator arms) in specific operating parameters for only part of the proposed procedure, and then switching the assignments during the procedure. In instances where a software interface is used, the software interface local to the operator (e.g., robotics user) may receive information from the management system and convey the recommended assignments to the operator.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. As used herein, with respect to measurements, terms of degree such as "about," "approximately," "substantially," etc. mean+/−5%. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A manipulator device management system, comprising:
- a manipulator device comprising a plurality of manipulator arms; and
- a control system comprising one or more processors and a memory, the memory comprising programmed instructions adapted to cause the one or more processors to perform operations comprising:
- selecting, for a first manipulator arm of the plurality of manipulator arms, a first assignment from a plurality of assignments available to the first manipulator arm, wherein the first assignment corresponds to a medical task to be performed by a manipulator arm, the medical task designating a location for the first manipulator arm with respect to a patient or a first pose of the first manipulator arm with respect to the patient,
- causing the first manipulator arm to adopt the first assignment, wherein the first assignment is available to at least two manipulator arms of the plurality of manipulator arms, and wherein selecting the first assignment comprises selecting from the plurality of assignments based on historical data of the plurality of manipulator arms by determining an amount of previous use of the first manipulator arm based on the historical data, and
- selecting, based on the historical data, a second assignment of a second manipulator arm of the plurality of manipulator arms, such that a less used manipulator arm of the first and second manipulator arms is paired with a more demanding assignment of the first and second assignments, wherein the more demanding assignment is associated with a higher load resulting in greater wear on a manipulator arm.

2. The management system of claim 1, wherein the historical data comprises usage data of the plurality of manipulator arms.

3. The management system of claim 1, wherein the operations further comprise: identifying the less used manipulator arm by using the historical data to determine at least one parameter selected from the group consisting of:

a duration of use of the first manipulator arm;

a number of uses of the first manipulator arm;

a wear amount of the first manipulator arm;

previous medical tasks performed by the first manipulator arm; and previous instruments driven by the first manipulator arm.

4. The management system of claim 1, wherein the operations further comprise: identifying the less used manipulator arm by using the historical data to determine an amount of use of a component of the first manipulator arm.

5. The management system of claim 1, wherein the historical data comprises performance test data of the plurality of manipulator arms.

6. The management system of claim 1, wherein the operations further comprise:

obtaining information about instrument types to be used with the manipulator device; and determining the plurality of assignments based on the information.

7. The management system of claim 1, wherein the operations further comprise:

obtaining information about the medical task to be performed with the manipulator device; and determining the plurality of assignments based on the information.

8. The management system of claim 7, wherein the operations further comprise:

designating, based on the historical data and the information about the medical task, one or more manipulator arms of the plurality of manipulator arms not to be used in the medical task.

9. The management system of claim 1, wherein causing the first manipulator arm to adopt the first assignment comprises providing an instruction to a user of the manipulator device management system to configure the first manipulator arm in accordance with the first assignment.

10. The management system of claim 1, wherein causing the first manipulator arm to adopt the first assignment comprises: commanding the manipulator device to configure the first manipulator arm in accordance with the first assignment.

11. A method of operating a manipulator device comprising a plurality of manipulator arms, the method comprising:

selecting, for a first manipulator arm of the plurality of manipulator arms, a first assignment from a plurality of assignments available to the first manipulator arm, wherein the first assignment corresponds to a medical task to be performed by a manipulator arm, the medical task designating a location for the first manipulator arm with respect to a patient or a first pose of the first manipulator arm with respect to the patient, causing the first manipulator arm to adopt the first assignment, wherein the first assignment is available to at least two manipulator arms of the plurality of manipulator arms, and wherein selecting the first assignment comprises selecting from the plurality of assignments based on historical data of the plurality of manipulator arms by determining an amount of previous use of the first manipulator arm based on the historical data, and selecting, based on the historical data, a second assignment of a second manipulator arm of the plurality of manipulator arms, such that a less used manipulator arm of the first and second manipulator arms is paired with a more demanding assignment of the first and second assignments, wherein the more demanding assignment is associated with a higher load resulting in greater wear on a manipulator arm.

12. The method of claim 11, wherein the historical data comprises performance test data of the plurality of manipulator arms.

13. The method of claim 11, further comprising:

obtaining information about instrument types to be used with the manipulator device or about the medical task to be performed with the manipulator device; and determining the plurality of assignments based on the information.

14. A non-transitory machine-readable medium or media comprising instructions that, when executed by one or more processors of a device comprising a plurality of manipulator arms, causes the one or more processors to perform a method comprising:

selecting, for a first manipulator arm of the plurality of manipulator arms, a first assignment from a plurality of assignments available to the first manipulator arm, wherein the first assignment corresponds to a medical task to be performed by a manipulator arm, the medical task designating a location for the first manipulator arm with respect to a patient or a first pose of the first manipulator arm with respect to the patient, causing the first manipulator arm to adopt the first assignment, wherein the first assignment is available to at least two manipulator arms of the plurality of manipulator arms, and wherein selecting the first assignment comprises selecting from the plurality of assignments based on historical data of the plurality of manipulator arms by determining an amount of previous use of the first manipulator arm based on the historical data, and selecting, based on the historical data, a second assignment of a second manipulator arm of the plurality of manipulator arms, such that a less used manipulator arm of the first and second manipulator arms is paired with a more demanding assignment of the first and second assignments, wherein the more demanding assignment is associated with a higher load resulting in greater wear on a manipulator arm.

* * * * *